(12) United States Patent
Barbour et al.

(10) Patent No.: US 11,147,815 B2
(45) Date of Patent: Oct. 19, 2021

(54) COMPOSITIONS AND METHODS FOR TREATING DISEASES ASSOCIATED WITH UNCONTROLLED INFLAMMATORY RESPONSES

(71) Applicant: SF17 THERAPEUTICS, INC., Oakland, CA (US)

(72) Inventors: Jason Barbour, Oakland, CA (US); David Ott, San Francisco, CA (US)

(73) Assignee: Synkrino Biotherapeutics, Inc.

( * ) Notice: Subject to any disclaimer, the term of this patent is extended or adjusted under 35 U.S.C. 154(b) by 0 days.

(21) Appl. No.: 16/642,362

(22) PCT Filed: Aug. 21, 2019

(86) PCT No.: PCT/US2019/047597
§ 371 (c)(1),
(2) Date: Feb. 26, 2020

(87) PCT Pub. No.: WO2020/041533
PCT Pub. Date: Feb. 27, 2020

(65) Prior Publication Data
US 2021/0251993 A1     Aug. 19, 2021

Related U.S. Application Data

(60) Provisional application No. 62/720,867, filed on Aug. 21, 2018.

(51) Int. Cl.
| | |
|---|---|
| *A61K 31/495* | (2006.01) |
| *A61K 31/496* | (2006.01) |
| *A61K 31/513* | (2006.01) |
| *A61K 31/435* | (2006.01) |
| *A61P 19/02* | (2006.01) |
| *A61P 35/00* | (2006.01) |
| *A61K 31/515* | (2006.01) |
| *A61K 31/437* | (2006.01) |
| *A61K 31/50* | (2006.01) |
| *A61K 45/06* | (2006.01) |
| *C12Q 1/6883* | (2018.01) |
| *G16B 40/00* | (2019.01) |
| *G16B 25/10* | (2019.01) |
| *A61P 37/06* | (2006.01) |

(52) U.S. Cl.
CPC .......... *A61K 31/515* (2013.01); *A61K 31/437* (2013.01); *A61K 31/496* (2013.01); *A61K 31/50* (2013.01); *A61K 45/06* (2013.01); *A61P 19/02* (2018.01); *A61P 37/06* (2018.01); *C12Q 1/6883* (2013.01); *G16B 25/10* (2019.02); *G16B 40/00* (2019.02); *C12Q 2600/158* (2013.01)

(58) Field of Classification Search
CPC .. A61K 31/495; A61K 31/496; A61K 31/513; A61K 31/435; A61P 19/02; A61K 35/00
USPC ............ 514/247, 254.09, 269, 292, 303
See application file for complete search history.

(56) References Cited

U.S. PATENT DOCUMENTS

2018/0163202 A1   6/2018 Yang et al.

FOREIGN PATENT DOCUMENTS

| WO | 2016/138286 A1 | 9/2016 |
| WO | 2018/023108 A1 | 2/2018 |

OTHER PUBLICATIONS

International Search Report and Written Opinion in International Application No. PCT/US2019/047597, dated Dec. 18, 2019.
Cartozzolo et al., "TRIM8: Making the Right Decision between the Oncogene and Tumour Suppressor Role," Genes, vol. 8, No. 354, Nov. 28, 2017, pp. 1-14.
Stewart et al., "E2 Enzymes: more than just middle men," Cell Research, vol. 26, No. 4, Apr. 2016, pp. 423-440.

*Primary Examiner* — Raymond J Henley, III
(74) *Attorney, Agent, or Firm* — Cognition IP, P.C.; Edward Steakley

(57) ABSTRACT

Methods of treating, controlling or managing diseases associated with uncontrolled inflammatory responses are provided. These methods comprise the administration of small molecule compounds that alter the activity of Tripartite motif containing 8 (TRIM8) in blood monocytes. Also provided are pharmaceutical compositions that comprise small molecule compounds that specifically target the E2-RING domain or the RING-RING dimerization domain of TRIM8 for the treatment, control or management of diseases associated with uncontrolled inflammatory responses.

36 Claims, 20 Drawing Sheets

E2-site top hit example

Top compounds form specific
- hydrogen bond with Tyr59
- Exensive hydrophobics with Ile17

Ile17

- Steric Clashes with E2

COMPOSITIONS AND METHODS FOR TREATING DISEASES ASSOCIATED WITH UNCONTROLLED INFLAMMATORY RESPONSES

CROSS-REFERENCE TO RELATED APPLICATIONS

This application is a 35 U.S.C. § 371 national stage application of PCT International Application No. PCT/US2019/047597, filed Aug. 21, 2019, which claims the benefit of U.S. Provisional Application No. 62/720,867, filed Aug. 21, 2018, both of which are hereby incorporated by reference in their entirety.

FIELD

Provided herein are methods of treating, controlling or managing diseases associated with uncontrolled inflammatory responses in subjects in need thereof. The disclosed methods make use of small molecule inhibitors that alter the activity of Tripartite motif containing 8 (TRIM8) in blood monocytes. Also provided are pharmaceutical compositions that comprise small molecule inhibitors that specifically target the E2-RING domain or the RING-RING dimerization domain of TRIM8 for the treatment, control or management of diseases associated with uncontrolled inflammatory responses in subjects in need thereof. The pharmaceutical compositions may be administered orally, parenterally, intranasally or transdermally.

BACKGROUND

Tripartite motif containing 8 (TRIM8) is a member of the tripartite motif protein family, an E3 ubiquitin-protein ligase family. E3 ubiquitin-protein ligases are known to regulate protein stability and protein degradation. TRIM proteins play diverse roles in the cells and are characterized by the presence of conserved domains, including a RING (really interesting new gene) domain, one or two zinc-finger motifs named B-box domains, a Coiled Coil (CC) domain and an n-terminal domain. TRIM proteins are involved in a broad range of biological processes, and have important roles in differentiation, development, intracellular signaling, protein quality control, autophagy, and immune responses. TRIM proteins have been associated with the pathogenesis of tumors, the control of developmentally regulated differentiation, the control of inflammatory responses, the coordination of signaling through cytokine pathways to other proteins and the nucleus, and the control of cell "sternness," which is the degree to which a cell has differentiated past a stem cell-like state. Furthermore, many TRIM proteins are induced by type I and type II interferons (IFNs), suggesting that TRIM proteins have a role in anti-viral and anti-microbial systems. Mutations in the genes encoding certain TRIMs have been associated with human immunological diseases and developmental disorders. Moreover, several TRIM members are involved in cancer. The human TRIM8/GERP gene is ubiquitously expressed in adult tissues and in a variety of tumors, including anaplastic oligodendroglioma and glioblastoma. Expression of TRIM8 seems to decrease the repression of interferon-γ (IFN-γ) mediated by SOCS-1, a member of the suppressor of cytokine signaling (SOCS) family.

Systemic juvenile idiopathic arthritis (SJIA) is a childhood rheumatic condition typically characterized by spiking fever, transient rash, and arthritis. SJIA is a serious inflammatory illness in children. It is a rare disease (affecting less than 10,000 children in the U.S.), and its adult form is known as Still's Disease, which is also characterized by persistent high spiking fevers, joint pain, and rash. SJIA is treated with a combination of medications, often including corticosteroids and immune therapies. Subjects affected by the disease may alternate between periods of disease activity (flare) and inactivity (quiescence). The etiology of SJIA is unknown, but it is hypothesized that infectious agents trigger the disease in genetically susceptible individuals. SJIA is often treated with anti-interleukin-1 (IL-1), anti-interleukin-6 (IL-6), or anti-tumor necrosis factor (TNF) therapies. However, a common complication of such therapies is the development of Macrophage Activation Syndrome (MAS), a life-threatening systemic inflammatory attack on the body. Currently, there are no effective treatments for SJIA and Still's disease.

Sjögren's syndrome is a systemic autoimmune disease that affects the entire body. Along with symptoms of extensive dryness of the eyes and mouth, other serious complications include profound fatigue, chronic pain, joint pain, dysfunction of the kidneys, the gastrointestinal system, blood vessels, lungs, liver, pancreas, and the central nervous system, neuropathies, and lymphomas. While some people experience mild discomfort, others suffer debilitating symptoms that greatly impair their functioning. Currently, Sjögren's syndrome affects the life of four million Americans and it is one of the most prevalent autoimmune diseases. Nine out of 10 patients are women. Subjects affected by Sjögren's syndrome may also present other autoimmune connective tissue diseases, such as rheumatoid arthritis, lupus, or scleroderma. Currently, there is no effective treatment for Sjögren's syndrome.

Lack of response or loss of response to immune therapy, defined here to include the anti-IL-1 pathway, anti-IL-6 pathway and anti-TNF pathway therapies, is common among patients on long-term immune therapy for conditions with a chronic inflammatory component. This includes, but is not limited to, autoimmune disorders, such as Lupus (SLE), and Rheumatoid Arthritis, and an expanding range of clinical disorders with an inflammatory component. Subjects who lose response to immune therapy, or have sub-optimal response to therapy may experience disease relapse, or development of secondary inflammatory disorders, such as MAS described herein for SJIA, and others, which can be debilitating or lethal.

A need exists for an effective treatment of SJIA and prevention of possible complications related to MAS. A need also exists for an effective treatment of other diseases that are associated with uncontrolled inflammatory responses, such as Still's disease, Sjögren's syndrome and cancer. A need exists for treatments to prevent the failure of primary immune therapy, and to prevent the secondary inflammatory disorders that can occur among subjects on long-term immune therapy.

The present application presents a solution to the aforementioned challenges. In particular, provided herein are methods and compositions for treating diseases associated with the uncontrolled expression of proinflammatory cytokines, such as SJIA, that aim at reducing the expression of TRIM8.

SUMMARY

It is shown herein that a reduction in the expression of TRIM8 in a subject's blood monocytes dramatically diminishes the subject's response to cytokine stimulation through the IFN-1 pathway. Based on these findings, methods of treating, controlling or managing a disease associated with uncontrolled inflammatory response in a subject in need thereof are provided. The disclosed methods comprise altering the activity of TRIM8 in a subject's blood monocytes by administering to the subject a small molecule compound that binds the E2-RING binding site or the RING-RING dimerization binding site of TRIM8. In some examples, the small molecule compound binds the E2-RING binding site of TRIM8 and it comprises a compound comprising a tricyclic region linked to a ring region connected to side chains.

In some embodiments, the small molecule compound that binds the E2-RING binding site is a compound comprising the formula:

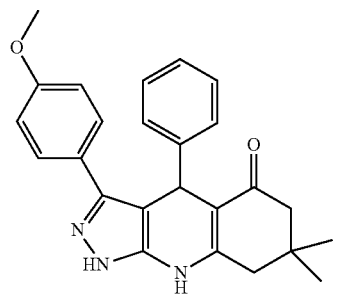 [SMILES: COc1ccc(-c2n[nH]c3c2C(c2ccccc2)C2=C(CC(C)(C)CC2=O)N3)cc1]

In some embodiments, the small molecule compound that binds the E2-RING binding site is a compound comprising the formula:

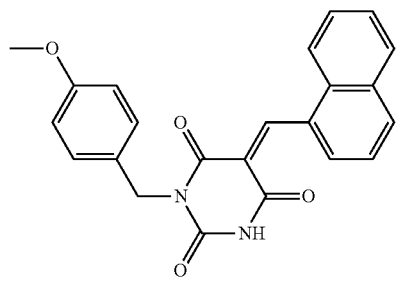 [SMILES: COc1ccc(CN2C(=O)NC(=O)/C(=C\c3cccc4ccccc34)C2=O)cc1]

In some embodiments, the small molecule compound that binds the E2-RING binding site is a compound comprising the formula:

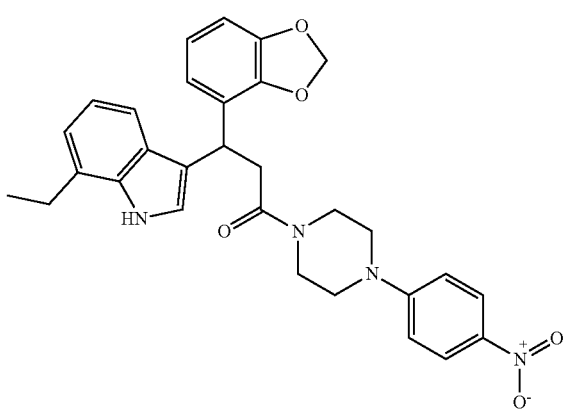

In other embodiments, the small molecule compound binds the RING-RING dimerization binding site of TRIM8 and it comprises a compound comprising a region comprising a terminal 6-member ring linked to a 5-member ring linked via a flexible linker to a central 6-member aromatic ring motif, which in turn is linked to another terminal 6-member ring.

In some embodiments, the small molecule compound binding the dimerization site of TRIM8 is a compound comprising the formula:

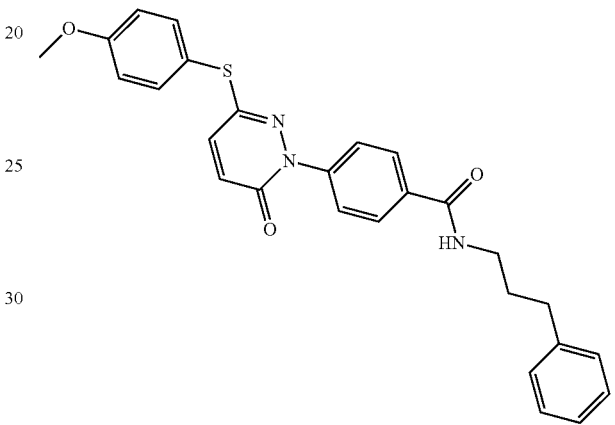

In some embodiments, the small molecule compound binding the dimerization site of TRIM8 is a compound comprising the formula:

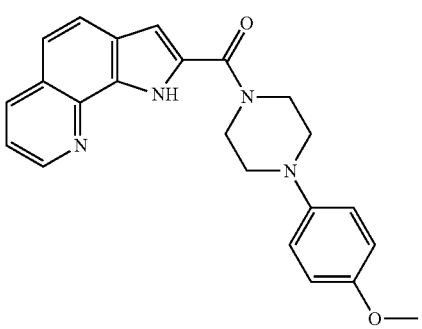 [SMILES: COc1ccc(N2CCN(C(=O)c3cc4ccc5cccnc5c4[nH]3)CC2)cc1]

In some embodiments, the small molecule compound binding the dimerization site of TRIM8 is a compound comprising the formula:

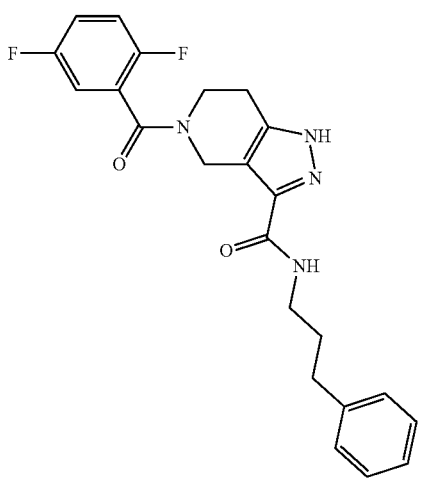 [SMILES: O=C(NCCCc1ccccc1)c1n[nH]c2c1CN(C(=O)c1cc(F)ccc1F)CC2]

In some examples, the pharmaceutical compositions that are administered according to the disclosed methods are formulated for oral, enteral, parenteral, intravenous, pulmonary, mucosal, sub-mucosal or transdermal administration.

In some examples, the pharmaceutical compositions may contain one or more pharmaceutically acceptable excipients, diluents, adjuvants, stabilizers, emulsifiers, preservatives, colorants, buffers, flavor-imparting agents and pharmaceutically acceptable carriers suitable for oral, enteral, parenteral, intravenous or transdermal administration.

In some examples, the pharmaceutical compositions that are administered according to the disclosed methods may further comprise one or more of a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

In some examples, the disease associated with uncontrolled inflammatory response is systemic juvenile idiopathic arthritis. In some examples, the disease associated with uncontrolled inflammatory response is Still's disease. In some examples, the disease associated with uncontrolled inflammatory response is Sjögren's syndrome. In some examples, the disease associated with uncontrolled inflammatory response is cancer.

In some examples, the disclosed method may comprise a step of identifying an uncontrolled inflammatory response in the subject prior to reducing abnormally elevated expression of TRIM8 in the subject's blood monocytes by administering to the subject a small molecule compound that binds the E2-RING binding site or the RING-RING dimerization binding site of TRIM8. In some examples, the step of identifying an uncontrolled inflammatory response in the subject may comprise detecting abnormally elevated expression of one or more cytokine, one or more cytokine receptor, one or more protein, or one or more signaling pathway. In some examples, the cytokine is one or more of CXCL9, CXCL10, CXCL11, S100A8, S100A9, S100A12, IL-1 beta, IL-6 or TNF. In some examples, the protein is TRIM8. In some examples, the signaling pathway is one or more of suppressor of cytokine signaling-1 (SOCS1) pathway, Janus tyrosine Kinase (JAK) pathway, or Signal Transducer and Activator of Transcription (STAT) pathway.

Also provided herein are pharmaceutical compositions that comprise small molecule compounds that specifically target the E2-RING domain or the RING-RING domain of TRIM8 for the treatment or management of diseases associated with uncontrolled inflammatory responses in subjects in need thereof.

In some examples, the small molecule compound binds the E2-RING binding site of TRIM8 and it comprises a compound comprising a tricyclic region linked to a ring region connected to side chains.

In some embodiments, the small molecule compound that binds the E2-RING binding site is a compound comprising the formula:

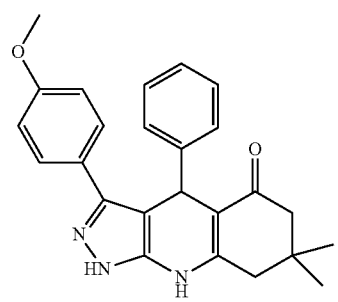 [SMILES: COc1ccc(-c2n[nH]c3c2C(c2ccccc2)C2=C(CC(C)(C)CC2=O)N3)cc1]

In some embodiments, the small molecule compound that binds the E2-RING binding site is a compound comprising the formula:

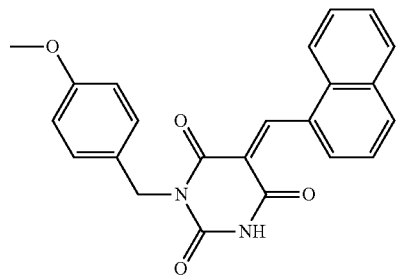 [SMILES: COc1ccc(CN2C(=O)NC(=O)/C(=C\c3cccc4ccccc34)C2=O)cc1]

In some embodiments, the small molecule compound that binds the E2-RING binding site is a compound comprising the formula:

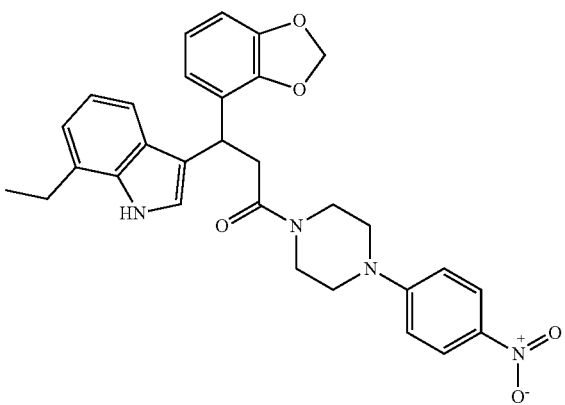

In some examples, the small molecule compound binds the RING-RING dimerization binding site of TRIM/8 and it comprises a compound comprising a region comprising a terminal 6-member ring linked to a 5-member ring linked via a flexible linker to a central 6-member aromatic ring motif, which in turn is linked to another terminal 6-member ring.

In some embodiments, the small molecule compound binding the dimerization site of TRIM8 is a compound comprising the formula:

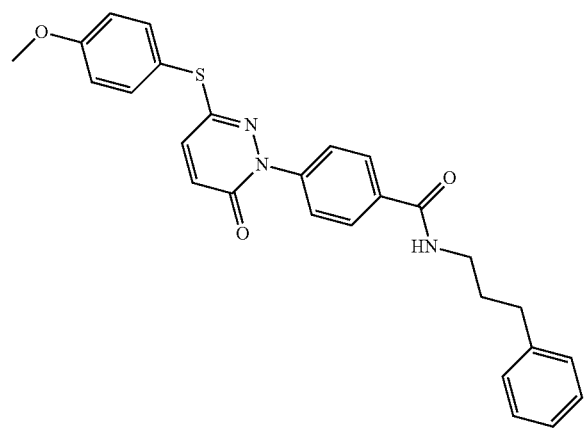 [SMILES: COc1ccc(Sc2ccc(=O)n(-c3ccc(C(=O)NCCCc4ccccc4)cc3)n2)cc1]

In some embodiments, the small molecule compound binding the dimerization site of TRIM8 is a compound comprising the formula:

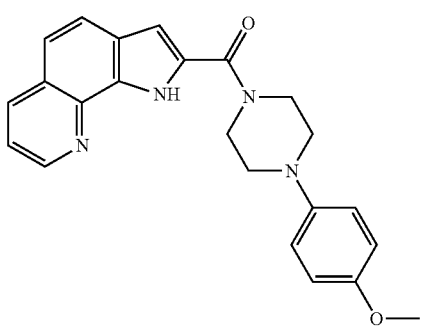 [SMILES: COc1ccc(N2CCN(C(=O)c3cc4ccc5cccnc5c4[nH]3)CC2)cc1]

In some embodiments, the small molecule compound binding the dimerization site of TRIM8 is a compound comprising the formula:

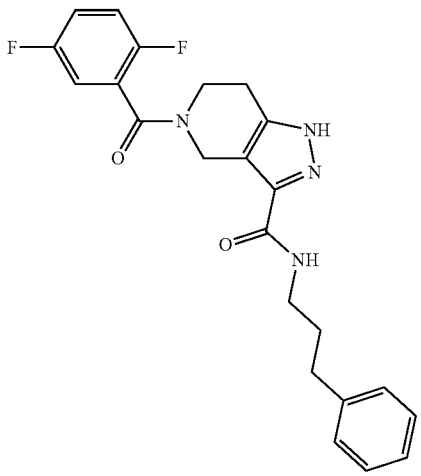 [SMILES: O=C(NCCCc1ccccc1)c1n[nH]c2c1CN(C(=O)c1cc(F)ccc1F)CC2]

In some examples, the disclosed pharmaceutical compositions are formulated for oral, enteral, parenteral, intravenous, mucosal, sub-mucosal or transdermal administration.

In some examples, the disclosed pharmaceutical compositions are formulated in form of a capsule, tablet, pill, powder, granule, dragee, lozenge or bead for oral administration in immediate release form, sustained release form or controlled release form.

In some examples, the disclosed pharmaceutical compositions are formulated in form of liquid emulsions, solutions, suspensions, syrups or elixirs for oral administration.

In some examples, the disclosed pharmaceutical compositions are formulated in form of injectable depot for parenteral administration.

In some examples, the disclosed pharmaceutical compositions are formulated in form of patch or hydrogel for transdermal application.

In some examples, the pharmaceutical compositions may contain one or more pharmaceutically acceptable excipients, diluents, adjuvants, stabilizers, emulsifiers, preservatives, colorants, buffers, flavor-imparting agents, a bacteriostatic agent, a fungistatic agent, emollients, plasticizers, permeation enhancers, antioxidants, pigments, lubricants, preservatives, wetting agents, salts, and any mixture thereof, and pharmaceutically acceptable carriers suitable for oral, enteral, parenteral, intravenous or transdermal administration.

In some examples, the disclosed pharmaceutical compositions may further comprise one or more of a chemotherapeutic agent, an immunosuppressive agent, an immunostimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteoinductive factor, an antibacterial agent or an antifungal agent.

In some examples, the disease associated with uncontrolled inflammatory response is systemic juvenile idiopathic arthritis. In some examples, the disease associated with uncontrolled inflammatory response is Still's disease. In some examples, the disease associated with uncontrolled inflammatory response is Sjögren's syndrome. In some examples, the disease associated with uncontrolled inflammatory response is cancer.

In some examples, a random forest classifier or other machine learning classifier may be used to determine whether a subject is a candidate for treatment with the disclosed pharmaceutical formulations.

The foregoing and other features of the disclosure will become more apparent from the following detailed description of several embodiments, which proceeds with reference to the accompanying figure.

DETAILED DESCRIPTION

Figure 1:
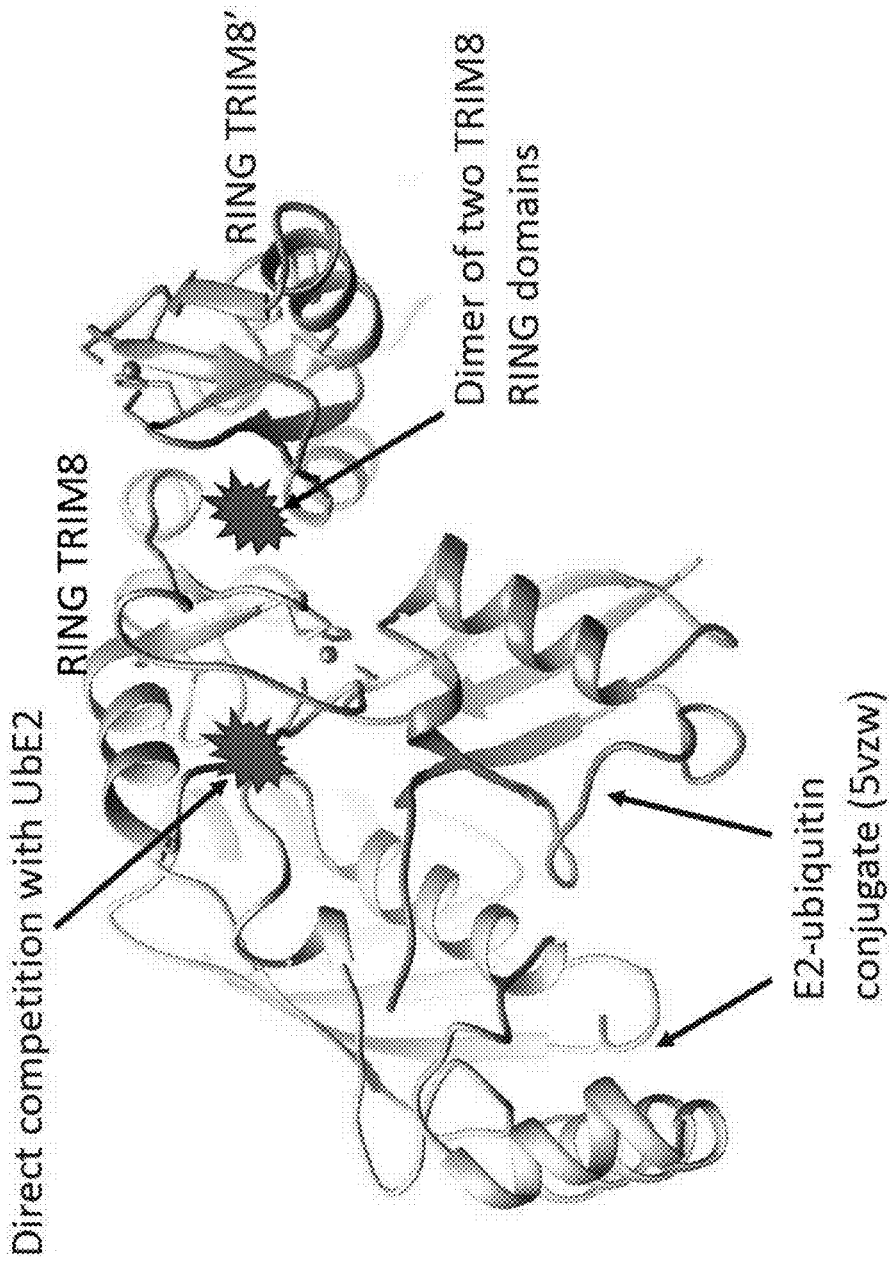
FIG. 1 provides a schematic representation of the two binding sites of TRIM8 targeted by the disclosed methods. The E2-RING site is upper left, and the RING-RING site is at top right.
Figure 2:
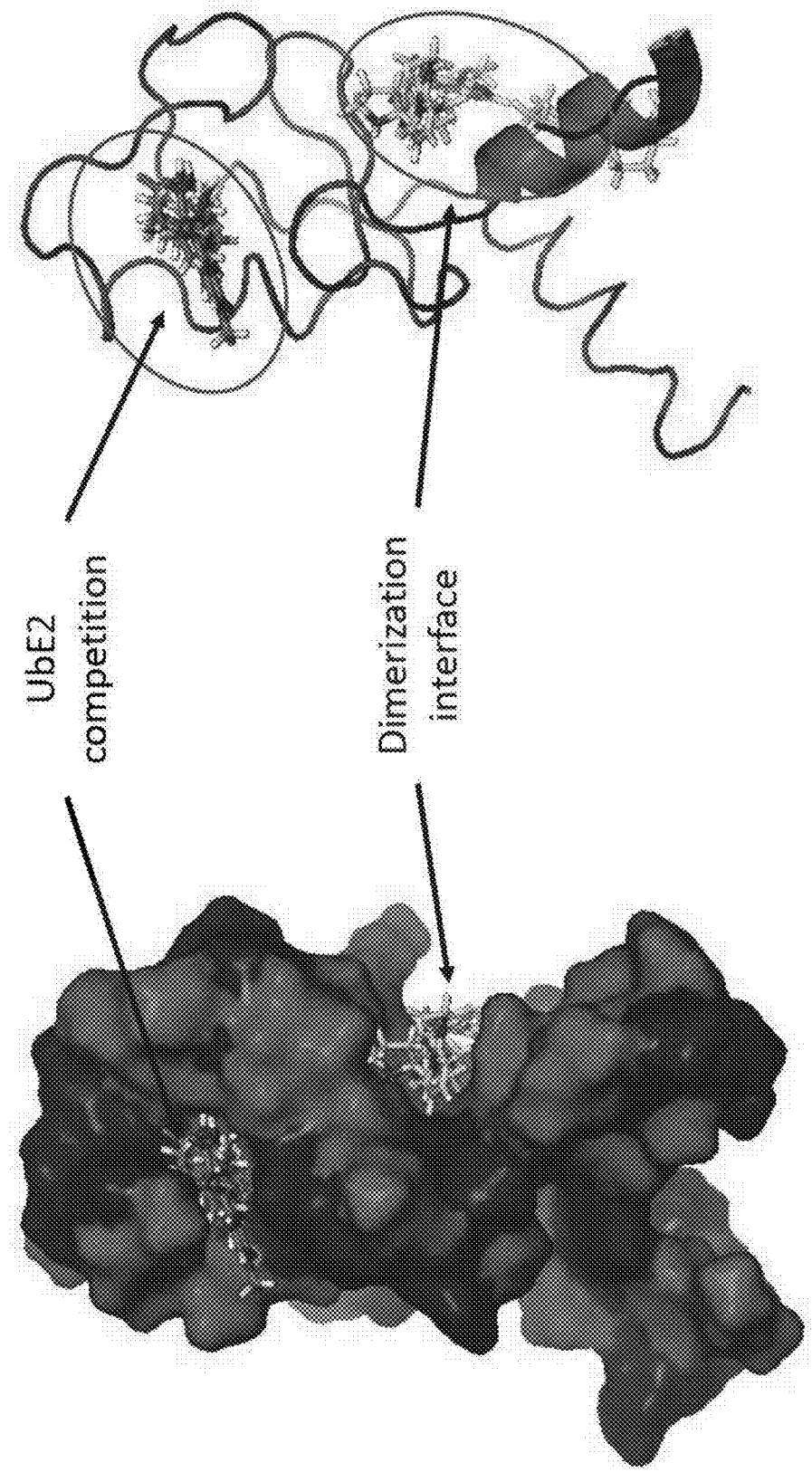
FIG. 2 provides an alternate view of the two binding sites of TRIM8 targeted by the disclosed methods. The E2-RING site is in the upper portion of the figure, and the RING-RING dimerization site is underneath.
Figure 3:
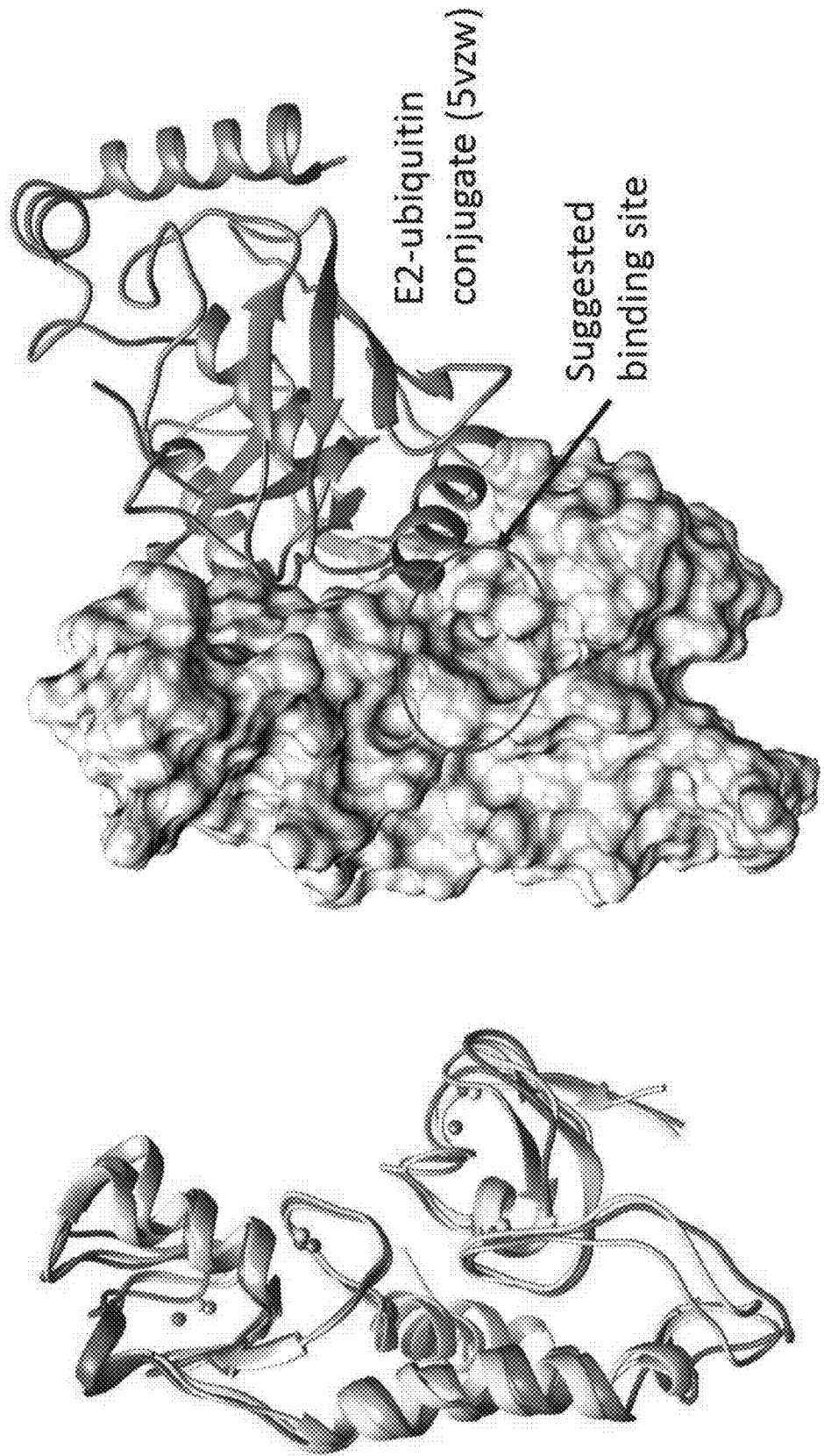
FIG. 3 provides a third view of the E2-RING binding site. The RING of TRIM8 is shown on the left side, as well as on the right side, and the E2 ubiquitin conjugate is shown on the right side, with the circle showing the binding site targeted by the disclosed small molecule inhibitors.
Figure 4:
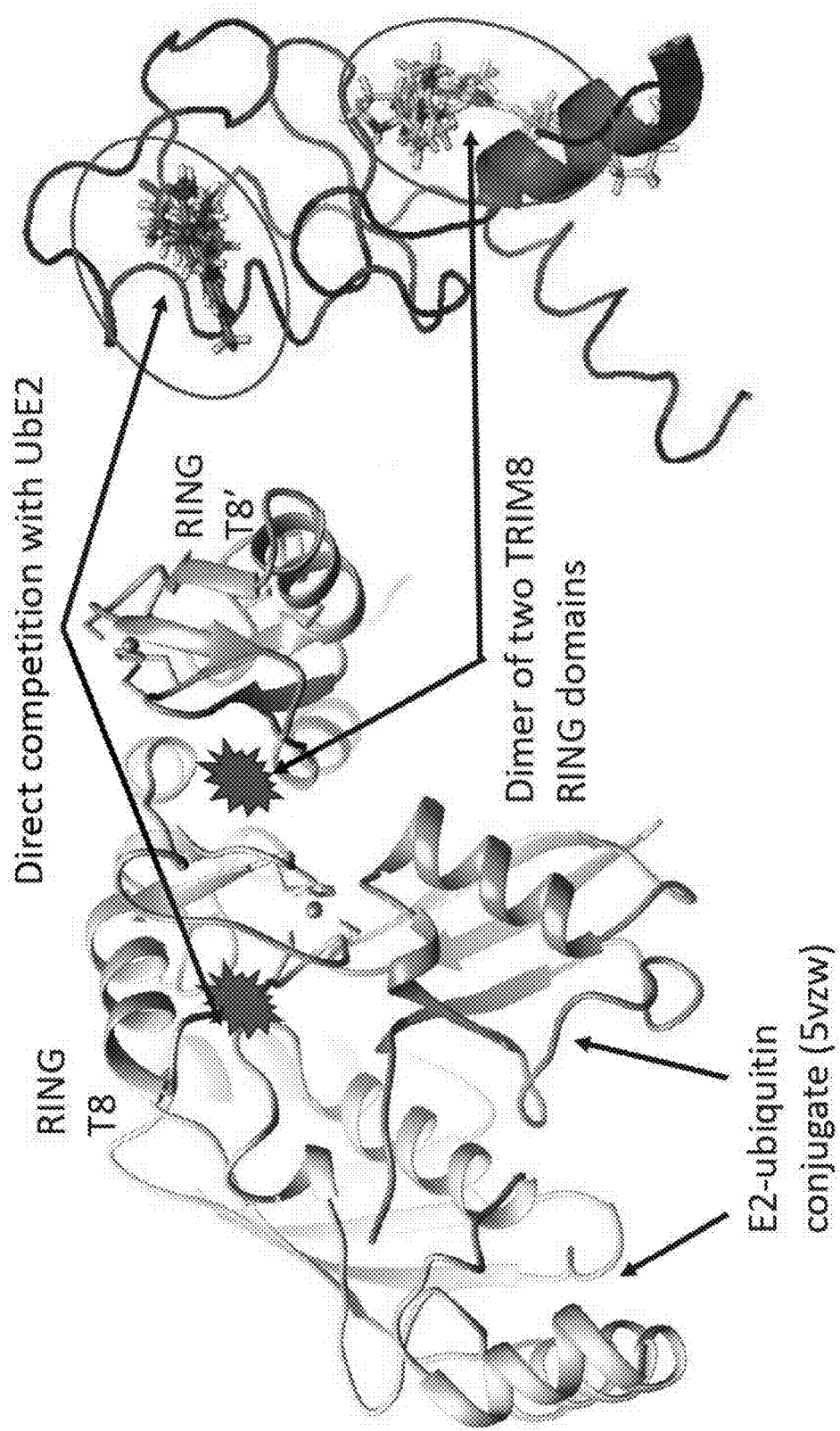
FIG. 4 shows the relationship between the ribbon model and the wireframe model, including the binding pockets.
Figure 5:
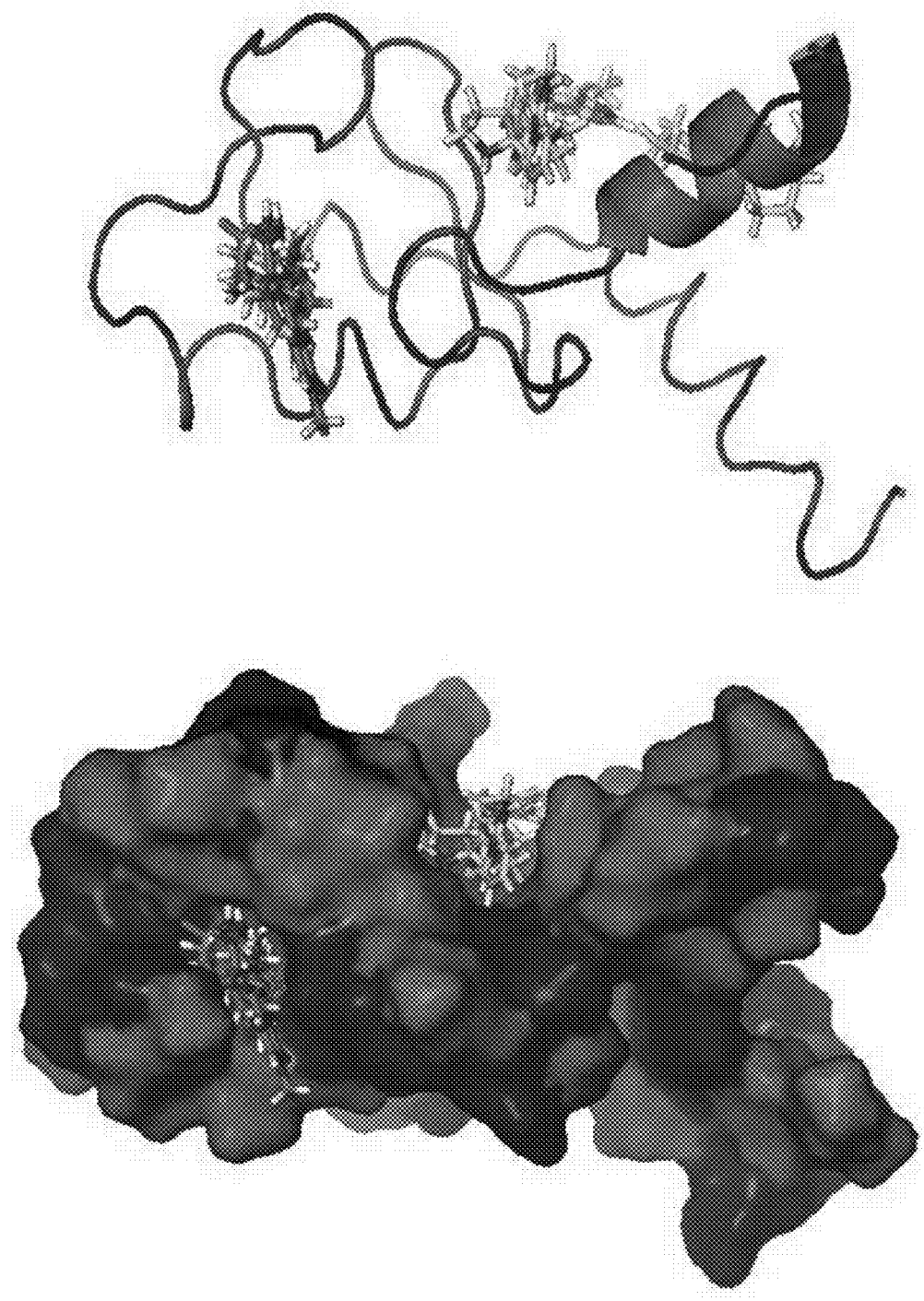
FIG. 5 provides a model showing the E2 ubiquitin competition site and the dimerization interface site.
Figure 6:
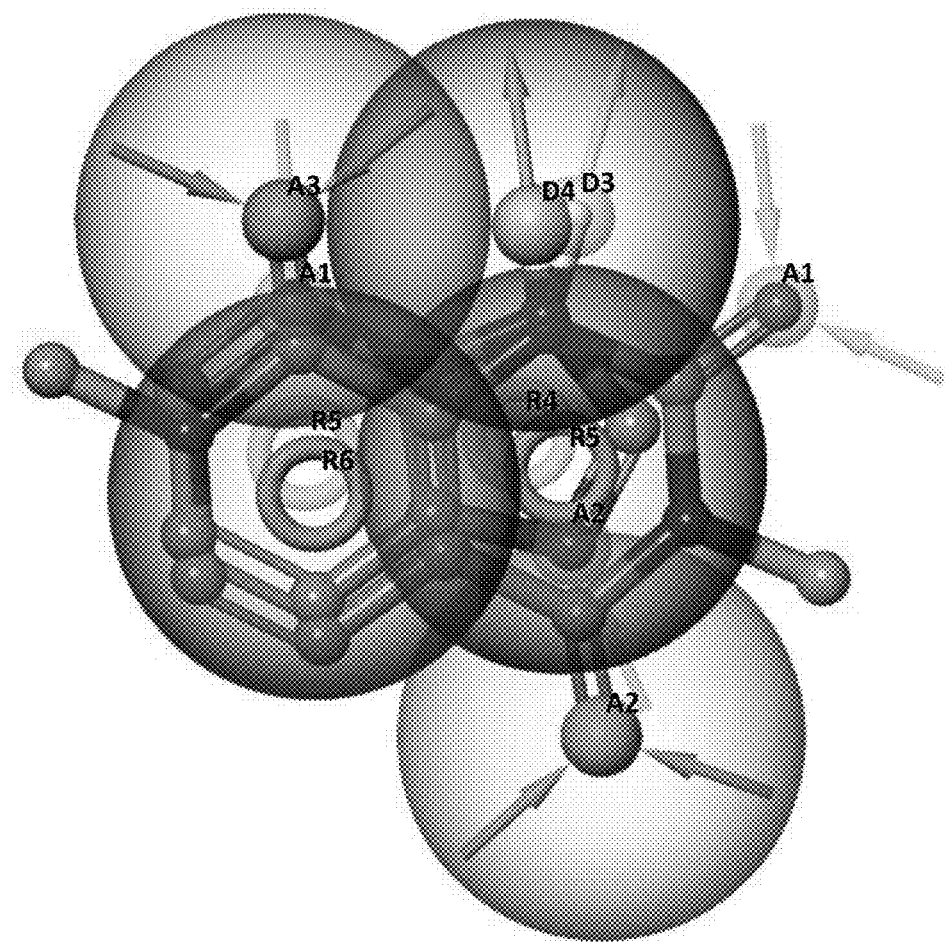
FIG. 6 provides a schematic view of the pharmacophore of the E2 binding motif of TRIM8, which is characterized by the presence of two joined, six member rings, and side chains.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entirety.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties for a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

To facilitate review of the various embodiments of this disclosure, the following explanations of specific terms are provided:

Administer or Apply: To provide or give a subject a composition, such as a pharmaceutical composition, by an effective route. Exemplary routes of administration include, but are not limited to, oral, enteral, parenteral, intravenous, mucosal, sub-mucosal or transdermal routes.

Analog: A compound having a structure similar to another, but differing from it, for example, in one or more atoms, functional groups, or substructure.

Anesthetic agent: An active agent that causes reduction or loss of sensation.

Antagonist: A molecule that, upon binding to a cell receptor, competes and/or interferes with one or more ligands binding the same receptor, and thus reduces or prevents a response elicited by those ligands.

Antibiotic: A chemical substance capable of treating bacterial infections by inhibiting the growth of, or by destroying existing colonies of bacteria and other microorganisms.

Anti-Fungal Agent: An active agent capable of inhibiting the growth of or destroying fungi.

Anti-inflammatory agent: An active agent that reduces inflammation and swelling.

Anti-Oxidant: An active agent that inhibits oxidation or reactions promoted by oxygen or peroxides.

Anti-Protozoal Agent: An active agent capable of inhibiting the growth of or destroying protozoa microorganisms.

Antipruritic Agent: An active agent that reduces, eliminates or prevents itching.

Anti-Viral Agent: An active agent that inhibits the replication of or destroys viruses.

Binding Site or Binding Domain: A region on a protein, DNA or RNA, to which specific molecules and/or ions (ligands) may form a chemical bond.

Characteristics of binding sites are chemical specificity, a measure of the types of ligands that will bond, and affinity, which is a measure of the strength of the chemical bond.

Chemotherapeutic agent or Chemotherapy: A chemical agent with therapeutic usefulness in the treatment of diseases characterized by abnormal cell growth. Such diseases include tumors, neoplasms, and cancer. In one example, a chemotherapeutic agent is a radioactive compound. In one example, a chemotherapeutic agent is a biologic, such as a monoclonal antibody. In some examples, a subject treated with an active agent using the disclosed methods, is, will be, or was previously treated with chemotherapy.

Contacting: Placement in direct physical association; includes both in solid and liquid form. Contacting can occur in vitro with isolated cells (for example in a tissue culture dish or other vessel) or in vivo by administering an active agent to a subject.

Control: A reference standard. In some examples, a control is a known value or range of values, such as one indicative of the presence or the absence of SJIA. In some examples, a control is a value or range of values, indicating a response in the absence of a therapeutic agent.

Cross-linked: A composition containing intramolecular and/or intermolecular crosslinks, whether arising through covalent or non-covalent bonding. "Non-covalent" bonding includes both hydrogen bonding and electrostatic (ionic) bonding.

CXCL9: Chemokine (C-X-C motif) ligand 9 is a small cytokine belonging to the (XC chemokine family that is also known as Monokine induced by gamma interferon (MIG). CXCL9 is a T-cell chemoattractant, which is induced by IFN-γ.

CXCL10: Chemokine (C-X-C motif) ligand 10, also known as Interferon gamma-induced protein 10 (I3-10) or small-inducible cytokine 1310, is secreted by monocytes, endothelial cells and fibroblasts in response to IFN-7.

CXCL11: Chemokine (C_X_C motif) ligand 11, also known as Interferon-inducible T-cell alpha chemoattractant (I-TAC) and Interferon-gamma-inducible protein 9 (IP-9), is expressed in leukocytes, the pancreas and liver. It is strongly induced by IFN-gamma and IFN-beta. CXCL11 is a chemotactic for T-cells.

Cytokine: A substance released by one cell population that acts on another cell as intercellular mediator. Examples of cytokines include, but are not limited to, lymphokines, monokines; interleukins (ILs) such as IL-1, IL-la, IL-2, IL-3, IL-4, IL-5, IL-6, IL-7, IL-8, IL-9, IL-11, IL-12, IL-15, including PROLEUKIN® rIL-2; a tumor necrosis factor such as TNF-α or TNF-β; and other polypeptide factors including LIF and kit ligand (KL).

Cytotoxic agent: A substance that inhibits or prevents the function of cells and/or causes destruction of cells.

Domain: A distinct functional and/or structural unit of a protein. A conserved domain refers to a domain that has been conserved during evolution During evolution, changes at specific positions of an amino acid sequence in the protein have occurred in a way that preserve the physico-chemical properties of the original residues, and hence the structural and/or functional properties of that region of the protein.

Drug or Active Agent: A chemical substance or compound that induces a desired pharmacological or physiological effect, and includes therapeutically effective, prophylactically effective, or systematically effective agents. The terms also encompass pharmaceutically acceptable, pharmacologically active derivatives and analogs of those active agents specifically mentioned herein, including, but not limited to, salts, esters, amides, prodrugs, active metabolites, inclusion complexes, analogs, and the like. Suitable active agents that may be incorporated into the pharmaceutical compositions provided herein include, but are not limited to, adrenergic agents; adrenocortical steroids; adrenocortical suppressants; alcohol deterrents; aldosterone antagonists; amino acids; ammonia detoxicants; anabolic agents; analeptic agents; analgesic agents; androgenic agents; anesthetic agents; anorectic compounds; anorexic agents; antagonists; anterior pituitary activators and anterior pituitary suppressants; anti-acne agents; anti-adrenergic agents; anti-allergic agents; anti-amebic agents; anti-androgen agents; anti-anemic agents; anti-anginal agents; anti-anxiety agents; anti-arthritic agents; anti-asthmatic agents and other respiratory drugs; anti-atherosclerotic agents; anti-bacterial agents; anti-cancer agents, including antineoplastic drugs, and anti-cancer supplementary potentiating agents; anticholinergics; anticholelithogenic agents; anti-coagulants; anti-coccidal agents; anti-convulsants; anti-depressants; anti-diabetic agents; anti-diarrheals; anti-diuretics; antidotes; anti-dyskinetics agents; anti-emetic agents; anti-epileptic agents; anti-estrogen agents; anti-fibrinolytic agents; anti-fungal agents; anti-glaucoma agents; antihelminthics; anti-hemophilic agents; anti-hemophilic Factor; anti-hemorrhagic agents; antihistamines; anti-hyperlipidemic agents; anti-hyperlipoproteinemic agents; antihypertensive agents; anti-hypotensives; anti-infective agents such as antibiotics and antiviral agents; anti-inflammatory agents, both steroidal and non-steroidal; anti-keratinizing agents; anti-malarial agents; antimicrobial agents; anti-migraine agents; anti-mitotic agents; anti-mycotic agents; antinauseants; antineoplastic agents; anti-neutropenic agents; anti-obsessional agents; anti-parasitic agents; antiparkinsonism drugs; anti-pneumocystic agents; anti-proliferative agents; anti-prostatic hypertrophy drugs; anti-protozoal agents; antipruritics; anti-psoriatic agents; antipsychotics; antipyretics; antispasmodics; anti-rheumatic agents; anti-schistosomal agents; anti-seborrheic agents; anti-spasmodic agents; anti-tartar and anti-calculus agents; anti-thrombotic agents; anti-tubercular agents; anti-tussive agents; anti-ulcerative agents; anti-urolithic agents; antiviral agents; GERD medications, anxiolytics; appetite suppressants; attention deficit disorder (ADD) and attention deficit hyperactivity disorder (ADHD) drugs; bacteriostatic and bactericidal agents; benign prostatic hyperplasia therapy agents; blood glucose regulators; bone resorption inhibitors; bronchodilators; carbonic anhydrase inhibitors; cardiovascular preparations including anti-anginal agents, anti-arrhythmic agents, beta-blockers, calcium channel blockers, cardiac depressants, cardiovascular agents, cardioprotectants, and cardiotonic agents; central nervous system (CNS) agents; central nervous system stimulants; choleretic agents; cholinergic agents; cholinergic agonists; cholinesterase deactivators; coccidiostat agents; cognition adjuvants and cognition enhancers; cough and cold preparations, including decongestants; depressants; diagnostic aids; diuretics; dopaminergic agents; ectoparasiticides; emetic agents; enzymes which inhibit the formation of plaque, calculus or dental caries; enzyme inhibitors; estrogens; fibrinolytic agents; fluoride anticavity/antidecay agents; free oxygen radical scavengers; gastrointestinal motility agents; genetic materials; glucocorticoids; gonad-stimulating principles; hair growth stimulants; hemostatic agents; herbal remedies; histamine H2 receptor antagonists; hormones; hormonolytics; hypnotics; hypocholesterolemic agents; hypoglycemic agents; hypolipidemic agents; hypotensive agents; HMGCoA reductase inhibitors; immunizing agents; immunomodulators; immunoregulators; immunostimulants; immunosuppressants; impotence therapy adjuncts; inhibitors; keratolytic agents; leukotriene inhibitors; LHRH agonists; liver disorder treatments; luteolysin agents; memory adjuvants; mental performance enhancers; metal chelators such as ethylenediaminetetraacetic acid, tetrasodium salt; mitotic inhibitors; mood regulators; mucolytics; mucosal protective agents; muscle relaxants; mydriatic agents; narcotic antagonists; nasal decongestants; neuroleptic agents; neuromuscular blocking agents; neuroprotective agents; nicotine; NMDA antagonists; non-hormonal sterol derivatives; nutritional agents, such as vitamins, essential amino acids and fatty acids; ophthalmic drugs such as antiglaucoma agents; oxytocic agents; pain relieving agents; parasympatholytics; peptide drugs; plasminogen activators; platelet activating factor antagonists; platelet aggregation inhibitors; post-stroke and post-head trauma treatments; potentiators; progestins; prostaglandins; prostate growth inhibitors; proteolytic enzymes as wound cleansing agents; prothyrotropin agents; psychostimulants; psychotropic agents; radioactive agents; regulators; relaxants; repartitioning agents; scabicides; sclerosing agents; sedatives; sedative-hypnotic agents; selective adenosine A1 antagonists; serotonin antagonists; serotonin inhibitors; serotonin receptor antagonists; steroids, including progestogens, estrogens, corticosteroids, androgens and anabolic agents; smoking cessation agents; stimulants; suppressants; sympathomimetics; synergists; thyroid hormones; thyroid inhibitors; thyromimetic agents; tranquilizers; tooth desensitizing agents; tooth whitening agents such as peroxides, metal chlorites, perborates, percarbonates, peroxyacids, and combinations thereof; unstable angina agents; uricosuric agents; vasoconstrictors; vasodilators including general coronary, peripheral and cerebral; vulnerary agents; wound healing agents; xanthine oxidase inhibitors; and the like.

Effective amount: The amount of an active agent (alone or with one or more other active agents) sufficient to induce a desired response, such as to prevent, treat, reduce and/or ameliorate an uncontrolled inflammatory response condition. Effective amounts of an active agent, alone or with one or more other active agents, can be determined in many different ways, such as assaying for a reduction in of one or more signs or symptoms associated with the condition, such as an uncontrolled inflammatory response condition, in the subject or measuring the level of one or more molecules associated with the condition to be treated.

Emulsifying Agents: Surfactants that reduce the interfacial tension between oil and water, minimizing the surface energy through formation of globules. Examples include, but are not limited to, glyceryl monostearate, methylcellulose, sodium lauryl sulfate, sodium oleate, sorbitan monopalmitate, sorbitan monostearate, sorbitan tristrearate, tragacanth, triethanolamine oleate, polyethylene sorbitan monolaurate, poloxamer, and any combination thereof.

Hydrogel: A water-swellable polymeric matrix that can absorb a substantial amount of water to form elastic gels. The matrix is a three-dimensional network of macromolecules held together by covalent or non-covalent crosslinks. Upon placement in an aqueous environment, dry hydrogels swell to the extent allowed by the degree of cross-linking.

Hydrogel Composition: A composition that either contains a hydrogel or is entirely composed of a hydrogel. Thus, "hydrogel compositions" encompass not only hydrogels per se but also compositions that comprise a hydrogel and one or more non-hydrogel components or compositions, e.g., hydrocolloids, which contain a hydrophilic component (which may contain or be a hydrogel) distributed in a hydrophobic phase.

Hydrophilic: A polymer, substance or compound that is capable of absorbing more than 10%/w of water at 100% relative humidity (rh).

Hydrophobic: A polymer, substance or compound that is capable of absorbing no more than 1%/w of water at 100% relative humidity (rh).

Hygroscopic: A polymer, substance or compound that is capable of absorbing more than 20 wt % of water at 100% relative humidity (rh).

Inhibiting a condition: Reducing, slowing, or even stopping the development of a condition, for example, in a subject who is at risk of developing or has a particular condition, such as an uncontrolled inflammatory response disease.

Interferon-gamma: IFN-γ, or type II interferon, is a cytokine inducing macrophages and Class II major histocompatibility complex (MHC) molecule expression.

Aberrant IFNγ expression is associated with a number of autoinflammatory and autoimmune diseases. IFNγ is produced predominantly by natural killer (NK) and natural killer T (NKT) cells as part of the innate immune response, and by CD4 Th1 and CD8 cytotoxic T lymphocyte (CTL) effector T cells once antigen-specific immunity develops.

Interferon-type I: a large group of interferon proteins that bind to interferon receptors and regulate the activity of the immune system.

Keratolytic Agent: An agent that that thins or softens the skin. Exemplary keratolytic agents include urea, lactic acid, allantoin, benzoyl peroxide, salicyclic acid, sulfur, tretinoin, fluorouracil, trichloroacetic acid, and glycolic acid.

Lipophilic: A substance or compound that has an affinity for a non-polar environment compared to a polar or aqueous environment.

Localized application: The application of an active agent in a particular location in the body.

Monocytes: The largest type of leukocytes or white blood cells, which can differentiate into macrophages and myeloid lineage dendritic cells. Monocytes are produced by the bone marrow from monoblasts, which differentiate from hematopoietic stem cells. Monocytes circulate in the bloodstream for about one to three days and then typically move into tissues throughout the body where they differentiate into macrophages and dendritic cells. Monocytes and their macrophage and dendritic-cell progeny serve three main functions in the immune system: phagocytosis, antigen presentation, and cytokine production. Phagocytosis is the process of uptake of microbes and particles followed by digestion and destruction of this material. Monocytes are also capable of killing infected host cells via antibody-dependent cell-mediated cytotoxicity.

Mucosa: A membrane that lines various cavities in the body and covers the surface of internal organs. It consists of one or more layers of epithelial cells overlying a layer of loose connective tissue. The mucosa is mostly of endodermal origin and is continuous with the skin at various body openings such as the eyes, ears, inside the nose, inside the mouth, lip, vagina, the urethral opening and the anus. Some mucous membranes secrete mucus, a thick protective fluid. The function of the membrane is to stop pathogens and dirt from entering the body and to prevent bodily tissues from becoming dehydrated.

Mucosal Administration: Administration through the mouth, nose, vagina, eyes and ears of a subject.

Oil: Any fatty substance that is in liquid form at room temperature (25° C.) and at atmospheric pressure (760 mmHg). An oily phase in a pharmaceutical composition may comprise at least one polar or apolar hydrocarbon-based oil.

Oral: oral administration includes food, beverages, drinks, soups, baked goods, syrups, oral pharmaceutical compositions, nutraceutical formulations, and the like. Liquid dosage forms for oral administration include, but are not limited to, pharmaceutically acceptable emulsions, solutions, suspensions, syrups and elixirs.

Parenteral: a type of administration that includes subcutaneous injections, intravenous, intramuscular, intrasternal injection or infusion techniques. Compositions for parenteral injection comprise pharmaceutically acceptable sterile aqueous or nonaqueous solutions, dispersions, suspensions or emulsions as well as sterile powders for reconstitution into sterile injectable solutions or dispersions prior to use.

Permeation Enhancer: A natural or synthetic molecule that facilitates the transport of co-administered active agents across biological membranes. pH Modifier: A molecule or buffer used to achieve desired pH control in a formulation. Exemplary pH modifiers include acids (e.g., acetic acid, adipic acid, carbonic acid, citric acid, fumaric acid, phosphoric acid, sorbic acid, succinic acid, tartaric acid, basic pH modifiers (e.g., magnesium oxide, tribasic potassium phosphate), and pharmaceutically acceptable salts thereof.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of the compositions herein disclosed. The nature of the carrier can depend on the particular mode of administration being employed. For instance, oral applications usually include pharmaceutically and physiologically acceptable fluids such as water, physiological saline, balanced salt solutions, aqueous dextrose, glycerol or the like as a vehicle. In addition to biologically-neutral carriers, oral compositions may also contain minor amounts of non-toxic auxiliary substances, such as wetting or emulsifying agents, preservatives, and pH buffering agents and the like.

Plasticizer: A material that, when added to a polymer, imparts an increase in flexibility, workability, and other properties to the finished product. Exemplary plasticizers include, but are not limited to, glycerol, sorbitol, polyethylene glycol, polypropylene glycol, polyethylene-propylene glycol, and any combination thereof.

Polymer: Includes homopolymers, linear and branched polymer structures, crosslinked polymers, copolymers (which may or may not be crosslinked), block copolymers, alternating copolymers, random copolymers, and the like. Oligomers are polymers having a molecular weight below about 1000 Da.

Proinflammatory cytokines: cytokines produced predominantly by activated macrophages and involved in the upregulation of inflammatory reactions. Exemplary proinflammatory cytokines include, but are not limited to, IL-1β, IL-6, and TNF-α. IL-1β is released primarily by monocytes and macrophages during cell injury, infection, invasion, and inflammation. IL-1β expression is enhanced following crush injury to peripheral nerve and after trauma in microglia and astrocytes in the central nervous system (CNS), and can produce hyperalgesia following either intraperitoneal, intracerebroventricular or intraplantar injection. IL-6 plays a role in the neuronal reaction to nerve injury. There is evidence that IL-6 contributes to the development of neuropathic pain behavior following a peripheral nerve injury. TNF-α, also known as cachectin, is an inflammatory cytokine that acts on several different signaling pathways through two cell surface receptors, TNFR1 and TNFR2, to regulate apoptotic pathways, NF-kB activation of inflammation, and activate stress-activated protein kinases (SAPKs).

Sjögren's Syndrome: A chronic disorder in which white blood cells attack the moisture-producing glands. Typical symptoms are dry eyes and dry mouth, caused by lymphocytic infiltrates of lacrimal and salivary glands. The loss of tears and saliva may result in characteristic changes in the eyes (called aqueous tear deficiency or keratoconjunctivitis sicca) and in the mouth with deterioration of the teeth, increased oral infection, difficulty in swallowing, and painful mouth. Subjects may also have inflammation of the joints (arthritis), muscles (myositis), nerves (neuropathy), thyroid (thyroiditis), kidneys (nephritis), lungs, or other areas of the body, or lymph node swelling, and may experience fatigue and sleep disruption. It is one of the most prevalent autoimmune disorders, striking as many as four million Americans, mainly middle-aged women.

Skin: The largest organ in the body consisting of several layers. The skin plays an important role in biologic homeostasis, and is comprised of the epidermis and the dermis. The epidermis, which is composed of several layers beginning with the stratum corneum, is the outermost layer of the skin, and the deep dermis is the innermost skin layer. The skin has multiple functions, including thermal regulation, metabolic function (vitamin D metabolism), and immune functions. In humans, the usual thickness of the skin is 1-2 mm, although in some areas the skin may be more than 5 mm thick.

The epidermis provides the body's buffer zone against the environment and protection from trauma, excludes toxins and microbial organisms, and constitutes a semi-permeable membrane. The stratum corneum is an avascular, multilayer structure that functions as a barrier to the environment and prevents trans-epidermal water loss. Below the stratum corneum are the stratum lucidum, stratum granulosum, stratum germinativum, and stratum basale, each containing living cells with specialized functions. Dermal appendages, which include hair follicles, sebaceous and sweat glands, fingernails, and toenails, originate in the epidermis and protrude into the dermis hair follicles. The sebaceous glands are responsible for secretions that lubricate the skin, and sweat gland secretions control skin pH to prevent dermal infections. The sweat glands, dermal blood vessels, and small muscles control temperature on the surface of the body. Nerve endings in the skin include receptors for pain, touch, heat, and cold. The basement membrane separates and connects the epidermis and dermis. The dermis is a vascular structure that supports and nourishes the epidermis. In addition, there are sensory nerve endings in the dermis that transmit signals regarding pain, pressure, heat, and cold. The superficial dermis consists of extracellular matrix (collagen, elastin, and ground substances) and contains blood vessels, lymphatics, epithelial cells, connective tissue, muscle, fat, and nerve tissue. The vascular supply of the dermis is responsible for nourishing the epidermis and regulating body temperature. Fibroblasts are responsible for producing the collagen and elastin components of the skin, which give the skin its turgor. Fibronectin and hyaluronic acid are secreted by the fibroblasts. The deep dermis is located over the subcutaneous fat; it contains larger networks of blood vessels and collagen fibers to provide tensile strength. It also consists of fibroelastic connective tissue, which is composed mainly of collagen.

Skin Simulating Membrane: A semi-permeable membrane used to replicate the skin in diffusion testing.

Subject: A living multi-cellular vertebrate organism, a category that includes human and non-human mammals, as well as birds (such as chickens and turkeys), fish, and reptiles. Exemplary subjects include mammals, such as human and non-human primates, rats, mice, dogs, cats, rabbits, cows, pigs, goats, horses, and the like.

Surface or Body Surface: A surface located on the human body or within a body orifice. Thus, a "body surface" includes, by way of example, skin, teeth, skin or mucosal tissue, including the interior surface of body cavities that have a mucosal lining.

Systemic juvenile idiopathic arthritis (SJIA): A chronic disease in children characterized by a combination of arthritis and systemic inflammation. Its adult form is known as Still's Disease, which is also characterized by persistent high spiking fevers, joint pain, and rash. The course of the disease is typically persistent or polycyclic with periods of disease flare and quiescence in about 60% of affected subjects. SJIA is treated with a combination of medications, often including corticosteroids and immune therapies. The immunotherapy often includes anti-interleukin-1 (IL-1), anti-interleukin-6 (IL-6), or anti-tumor necrosis factor (TNF) therapies. However, a common complication of such therapies is the development of Macrophage Activation Syndrome (MAS), a life-threatening systemic inflammatory attack on the body. Currently, there are no effective treatments for SJIA and Still's disease.

Transdermal: A route of administration by which active ingredients are delivered across the skin for systemic distribution. Examples include transdermal patches for drug delivery.

TRIM8: The TRIM8/GERP protein is a member of the TRIM family defined by the presence of a common domain structure composed of a tripartite motif including a RING-finger, one or two B-box domains, and a coiled-coil motif. The TRIM8 gene maps on chromosome 10 within a region frequently found deleted and rearranged in tumors, and it transcribes a 3.0-kB mRNA. TRIM8 is found in murine and human tissues, in epithelial and lymphoid cells, and it can be induced by IFNγ. Evidence suggests that TRIM8 may be involved in inflammation and cancer. The X-ray crystal structure of TRIM8 is not known.

Under conditions sufficient to: A phrase that is used to describe any environment that permits the desired activity.

Water-Insoluble: A polymer, compound or composition with a solubility in water of less than 5%/w, less than 3%/w, or less than 1%/w, as measured in water at 20° C.

Water-Swellable: A polymer, substance or compound, that may absorb an amount of water greater than at least 25%/w of its own weight, or greater than at least 50%/w, upon immersion in an aqueous medium.

Method of Treating, Controlling or Managing a Disease Associated with Uncontrolled Inflammatory Response The present inventors have identified TRIM8 as a major factor in the development of Macrophage Activation Syndrome (MAS), a life-threatening systemic inflammatory attack on the human body, in children affected by systemic juvenile idiopathic arthritis (SJIA), and in subjects with other diseases associated with uncontrolled inflammatory response, such as Sjögren's Syndrome, Still's Disease and cancer. Currently, there are no effective treatments for MAS.

Based on these findings, the present inventors developed computational models of the TRIM8 molecule, and identified two regions on the TRIM8 protein as suitable targets for the binding of small molecule compounds in order to modify TRIM8 activity: an E2-RING binding site and a RING-RING dimerization binding site.

TRIM8 is a member of the tripartite motif protein family, an E3 ubiquitin-protein ligase family. E3 ubiquitin-protein ligases are known to regulate protein stability and protein degradation. Therefore, a first strategy is provided herein, which aims at blocking the assembly of TRIM8 into its macromolecular complex including the E2 ligase, to prevent the degradation of proteins that are targeted by TRIM8, such as Suppressor Of Cytokine Signaling 1 (SOCS1), Protein Inhibitor Of Activated STAT 3 (PIAS3) and Transforming growth factor beta-activated kinase 1 (TAK1, also known as REF). The activities of these proteins are mediated by multiple cytokine signaling pathways, such as IL-1, IL-6 and TNF receptors, which in turn activate the IFN-I pathway. To this end, small molecule compounds were identified and are disclosed herein, that bind the E2-RING binding site and modify TRIM8 interaction with its targeted proteins. These small molecule compounds binding the E2-RING binding site of TRIM8 are characterized by the presence of a tricyclic region linked to a ring region connected to side chains in their structure.

A second approach is also provided herein, that aims at preventing TRIM8 homodimerization, a process that activates TRIM8, by targeting the RING-RING dimerization domain of TRIM8 with small molecule inhibitors, and thus destabilize and degrade TRIM8. Small molecule inhibitors were therefore identified and are disclosed herein, that bind the RING-RING dimerization domain of TRIM8 protein. These small molecule inhibitors comprise a region comprising a terminal 6-member ring linked to a 5-member ring linked via a flexible linker to a central 6-member aromatic ring motif, which in turn is linked to another terminal 6-member ring.

The present inventors unexpectedly and surprisingly found that a modification in the activity of TRIM8 in a subject's blood monocytes dramatically diminishes the subject's response to cytokine stimulation through the IFN-1 pathway. Based on these findings, a method of treating, controlling or managing a disease associated with uncontrolled inflammatory response in a subject in need thereof is provided. The method comprises altering the activity of TRIM8 in the subject's blood monocytes by administering to the subject a small molecule compound that binds the E2-RING binding site or the RING-RING dimerization binding site of TRIM8.

In some embodiments, the small molecule compound that binds the E2-RING binding site is a compound comprising the formula:

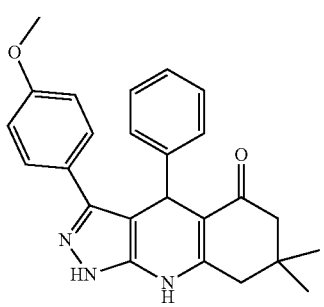 [SMILES: COc1ccc(-c2n[nH]c3c2C(c2ccccc2)C2=C(CC(C)(C)CC2=O)N3)cc1]

In some embodiments, the small molecule compound that binds the E2-RING binding site is a compound comprising the formula:

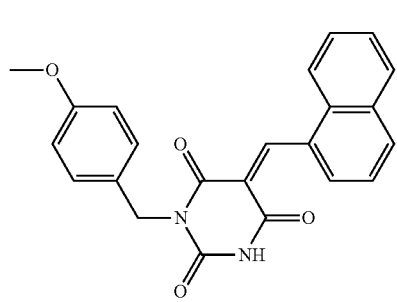 [SMILES: COc1ccc(CN2C(=O)NC(=O)/C(=C\c3cccc4ccccc34)C2=O)cc1]

In some embodiments, the small molecule compound that binds the E2-RING binding site is a compound comprising the formula:

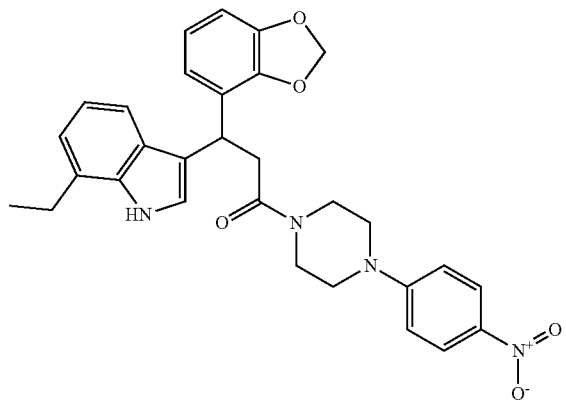 [SMILES: CCc1cccc2c(C(CC(=O)N3CCN(c4ccc([N+](=O)[O-])cc4)CC3)c3cccc4c3OCO4)c[nH]c12]

In some embodiments, the small molecule inhibitor binding the dimerization site of TRIM8 is a compound comprising the formula:

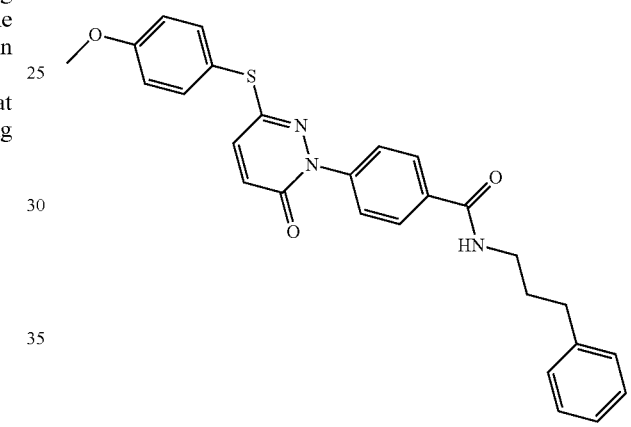

In some embodiments, the small molecule inhibitor binding the dimerization site of TRIM8 is a compound comprising the formula:

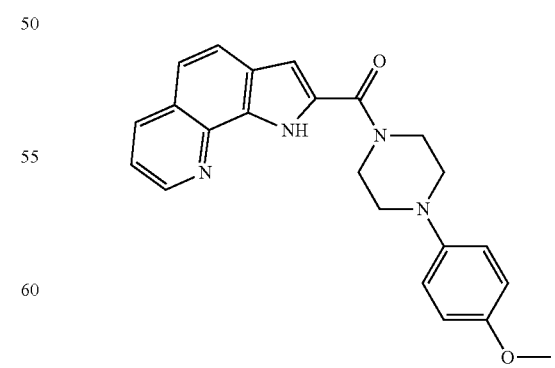

In some embodiments, the small molecule inhibitor binding the dimerization site of TRIM8 is a compound comprising the formula:

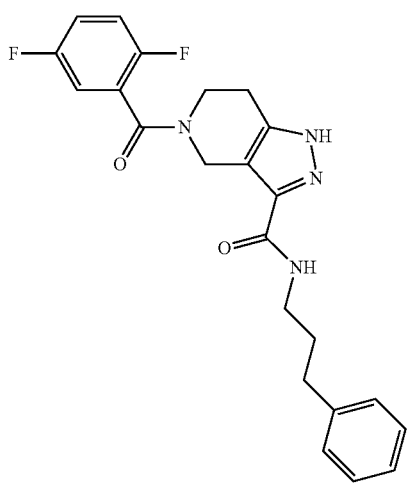 [SMILES: O=C(NCCCc1ccccc1)c1n[nH]c2c1CN(C(=O)c1cc(F)ccc1F)CC2]

Pharmaceutical compositions administered according to the disclosed methods may be formulated for oral, enteral, parenteral, intravenous, pulmonary, mucosal, sub-mucosal or transdermal administration, and may contain one or more pharmaceutically acceptable excipients, diluents, adjuvants, stabilizers, emulsifiers, preservatives, colorants, buffers, flavor-imparting agents and pharmaceutically acceptable carriers suitable for oral, enteral, parenteral, intravenous or transdermal administration.

The disclosed methods may further comprise administering one or more of a chemotherapeutic agent, an immuno-suppressive agent, an immuno-stimulatory agent, an antipyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

The methods provided herein may treat, control, manage or prevent diseases associated with uncontrolled inflammatory response such as, but not limited to, systemic juvenile idiopathic arthritis, Still's disease, Sjögren's syndrome and cancer.

In addition, the disclosed methods may comprise a step of identifying an uncontrolled inflammatory response in the subject prior to reducing abnormally elevated expression of TRIM8 in the subject's blood monocytes by the administration of small molecule inhibitors that binds the E2-RING binding site or the RING-RING dimerization binding site of TRIM8. The step of identifying an uncontrolled inflammatory response in a subject may comprise detecting abnormally elevated expression of one or more cytokines, one or more cytokine receptors, one or more proteins, or one or more signaling pathways.

Cytokines that may be detected by the disclosed method include, but are not limited to, CXCL9, CXCL10, CXCL11, S100A8, S100A9, S100A12, IL-1 beta, IL-6, TNF, or any combination thereof. Proteins include, but are not limited to, TRIM8. Signaling pathways include, but are not limited to, one or more of suppressor of cytokine signaling-1 (SOCS1) pathway, Janus tyrosine Kinase (JAK) pathway, Signal Transducer and Activator of Transcription (STAT) pathway, or any combination thereof.

Thus, the methods disclosed herein provide effective detection, treatment, control and/or management of diseases associated with uncontrolled inflammatory responses.

Pharmaceutical Compositions Comprising Small Molecule Inhibitors of TRIM8

Also provided herein are pharmaceutical compositions that comprise small molecule compounds that specifically target the E2-RING domain or the RING-RING dimerization domain of TRIM8 for the treatment, control or management of diseases associated with uncontrolled inflammatory responses in subjects in need thereof.

Small molecule compounds binding the E2-RING binding site of TRIM8 comprise compounds characterized by the presence of a tricyclic region linked to a ring region connected to side chains.

In some embodiments, the small molecule compound that binds the E2-RING binding site is a compound comprising the formula:

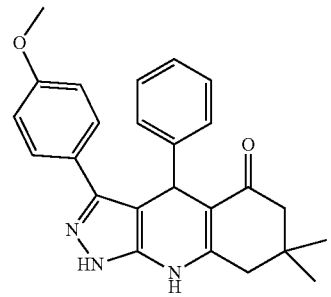 [SMILES: COc1ccc(-c2n[nH]c3c2C(c2ccccc2)C2=C(CC(C)(C)CC2=O)N3)cc1]

In some embodiments, the small molecule compound that binds the E2-RING binding site is a compound comprising the formula:

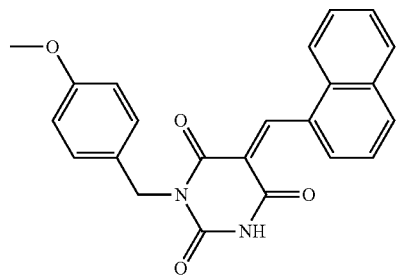 [SMILES: COc1ccc(CN2C(=O)NC(=O)/C(=C\c3cccc4ccccc34)C2=O)cc1]

In some embodiments, the small molecule compound that binds the E2-RING binding site is a compound comprising the formula:

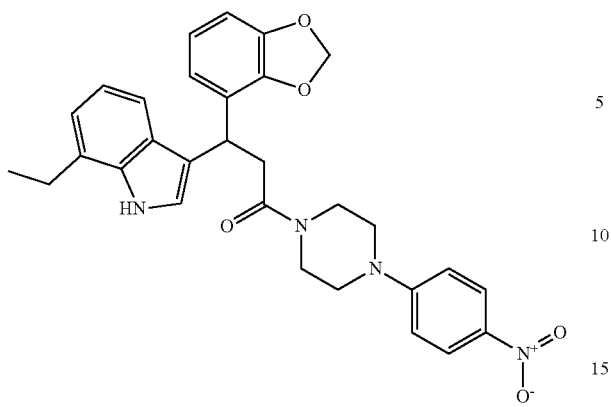

Small molecule inhibitors binding the RING-RING dimerization binding site of TRIM8 are compounds comprising a region comprising a terminal 6-member ring linked to a 5-member ring linked via a flexible linker to a central 6-member aromatic ring motif, which in turn is linked to another terminal 6-member ring.

In some embodiments, the small molecule inhibitor binding the dimerization site of TRIM8 is a compound comprising the formula:

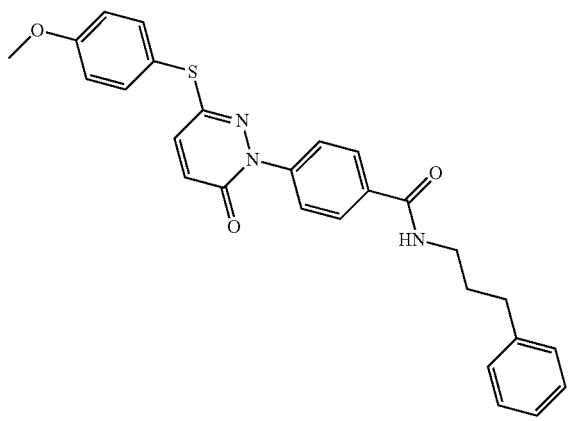 [SMILES: COc1ccc(Sc2ccc(=O)n(-c3ccc(C(=O)NCCCc4ccccc4)cc3)n2)cc1]

In some embodiments, the small molecule inhibitor binding the dimerization site of TRIM8 is a compound comprising the formula:

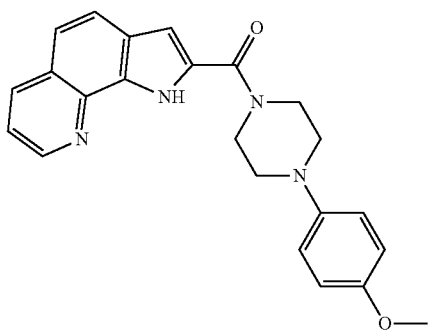 [SMILES: COc1ccc(N2CCN(C(=O)c3cc4ccc5cccnc5c4[nH]3)CC2)cc1]

In some embodiments, the small molecule inhibitor binding the dimerization site of TRIM8 is a compound comprising the formula:

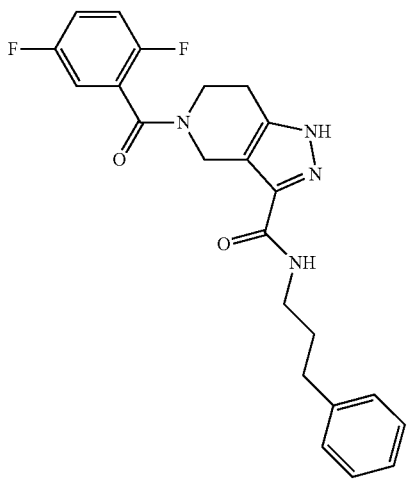 [SMILES: O=C(NCCCc1ccccc1)c1n[nH]c2c1CN(C(=O)c1cc(F)ccc1F)CC2]

The disclosed pharmaceutical compositions may be formulated for oral, enteral, parenteral, intravenous, mucosal, sub-mucosal or transdermal administration.

Solid dosage forms suitable for oral administration may include, but are not limited to, capsules, tablets, pills, powders, beads, lozenges, dragees, granules, or the like Such solid dosage forms may include at least one pharmaceutically acceptable excipient or carrier, such as sodium citrate or dicalcium phosphate; fillers or extenders, such as starches, lactose, sucrose, glucose, mannitol, and silicic acid; binders, such as, for example, carboxymethylcellulose, alginates, gelatin, polyvinylpyrrolidone, sucrose, and acacia; humectants, such as glycerol; disintegrating agents such as agar-agar, calcium carbonate, potato or tapioca starch, alginic acid, silicates and sodium carbonate; solution retarding agents such as paraffin; absorption accelerators, such as quaternary ammonium compounds; wetting agents such as, for example, acetyl alcohol and glycerol monostearate; absorbents such as kaolin and bentonite clay; lubricants, such as talc, calcium stearate, magnesium stearate, solid polyethylene glycols, sodium lauryl sulfate, and mixtures thereof, and buffering agents.

The disclosed solid pharmaceutical compositions for oral administration may be formulated in immediate release form, sustained release form or controlled release form, and coated using compounds that accelerate or decrease the release of the disclosed small molecule inhibitors. Thus, solid dosage forms may comprise enteric coatings, extended-release coatings, sustained-release coatings, delayed release coatings and immediate-release coatings. Methods used to coat solid dosage forms as well as the materials used to manufacture such coatings are well known in the pharmaceutical formulary art. Coating materials may include, but are not limited to, glyceryl monostearate, glyceryl distearate, polymeric substances and waxes.

Solid oral dosage forms may also be formulated as dietary compositions, and may comprise any ingestible preparation that contains the disclosed small molecule inhibitors mixed with a food product. The food product can be dried, cooked, boiled, lyophilized or baked, and may be in the form of breads, teas, juices, soups, cereals, salads, sandwiches, sprouts, vegetables, candies, pills, tablets, or the like.

Liquid dosage forms for oral administration may include, but are not limited to, pharmaceutically acceptable emulsions, solutions, suspensions, syrups and elixirs, and may contain inert diluents commonly used in the art. For instance, liquid formulations may contain water, alcohol, polyethylene glycol ethers, or any other pharmaceutically acceptable solvents; solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, and dimethyl formamide; oils, such as cottonseed, groundnut, corn, germ, olive, castor, and sesame oils; glycerol, tetrahydrofurfuryl alcohol, polyethylene glycols and fatty acid esters of sorbitan; adjuvants, such as wetting agents; emulsifying and suspending agents, such as ethoxylated isostearyl alcohols, polyoxyethylene sorbitol, sorbitan esters, microcrystalline cellulose, aluminum metahydroxide, bentonite, agar-agar, tragacanth, and mixtures thereof; sweetening, flavoring, perfuming agents, and any mixture thereof.

Parenteral administration may include subcutaneous injections, intravenous, intramuscular, intrasternal injection or infusion techniques. Micelles or liposomal suspensions for parenteral administration may be encapsulated with a variety of polymers, sugars, and chelating agents, to yield stable solid liposomal preparations or granules. Polymers for encapsulation may include crosslinked polymers, non-crosslinked polymers, or polymers dispersed within the crystalline structure of sugar starches or protein molecules. Granules may be further processed to yield sublingual films, suppositories, dispersible powder, tablets, gel capsules, or the like.

Compositions for parenteral injection may comprise pharmaceutically acceptable sterile aqueous or nonaqueous solutions, dispersions, suspensions or emulsions as well as sterile powders for reconstitution into sterile injectable solutions or dispersions prior to use. Examples of suitable aqueous and nonaqueous carriers, diluents, solvents or vehicles include, but are not limited to, water, ethanol, polyols, such as glycerol, propylene glycol, polyethylene glycol, and the like, carboxymethylcellulose and suitable mixtures thereof, vegetable oils, such as olive oil, and injectable organic esters, such as ethyl oleate. Proper fluidity can be maintained, for example, by the use of coating materials such as lecithin, by the maintenance of the required particle size in the case of dispersions, and by the use of surfactants. The disclosed pharmaceutical compositions for parenteral administration may also contain adjuvants such as, but not limited to, preservatives, wetting agents, emulsifying agents, and dispersing agents, isotonic agents, such as sugars, sodium chloride, and the like, and agents that delay absorption, such as aluminum monostearate and gelatin.

Injectable depot forms may be made by forming microcapsule matrices of the disclosed small molecule inhibitors in biodegradable polymers, such as polylactide-polyglycolide, poly(orthoesters) and poly(anhydrides). Depot injectable formulations may also be prepared by entrapping the disclosed small molecule inhibitors in liposomes or microemulsions compatible with body tissues. Injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

The disclosed pharmaceutical compositions may also be formulated in form of patch or hydrogel for transdermal application. Various additives, known to those skilled in the art, may be included in transdermal formulations. Examples of additives include, but are not limited to, solubilizers, skin permeation enhancers, preservatives, such as antioxidants, moisturizers, gelling agents, buffering agents, surfactants, emulsifiers, emollients, thickening agents, stabilizers, humectants, dispersing agents and pharmaceutical carriers. Examples of moisturizers include, but are not limited to, jojoba oil and evening primrose oil. Suitable skin permeation enhancers include, but are not limited to, lower alkanols, such as methanol ethanol and 2-propanol; alkyl methyl sulfoxides, such as dimethylsulfoxide (DMSO), decylmethylsulfoxide (C10 MSO) and tetradecylmethyl sulfoxide; pyrrolidones, urea; N,N-diethyl-m-toluamide; C2-C6 alkanediols; dimethyl formamide (DMF), N,N-dimethylacetamide (DMA) and tetrahydrofurfuryl alcohol. Examples of solubilizers include, but are not limited to, hydrophilic ethers, such as diethylene glycol monoethyl ether and diethylene glycol monoethyl ether oleate; polyoxy 35 castor oil, polyoxy 40 hydrogenated castor oil, polyethylene glycol (PEG), and polyethylene glycol derivatives, such as PEG-8 caprylic/capric glycerides; alkyl methyl sulfoxides, such as DMSO; pyrrolidones, DMA, and mixtures thereof.

Prevention and/or treatment of infections can be achieved by the inclusion of antibiotics, as well as various antibacterial and antifungal agents, for example, paraben, chlorobutanol, phenol sorbic acid, and the like, in the disclosed pharmaceutical compositions.

The disclosed pharmaceutical compositions may also be administered by a variety of other routes, including mucosal, subcutaneous and intramuscular administration, and may comprise a variety of carriers or excipients known in the formulary art, such as non-toxic solid, semisolid or liquid filler, diluent, encapsulating material and formulation auxiliaries that are pharmaceutically acceptable.

The disclosed pharmaceutical compositions may contain one or more pharmaceutically acceptable excipients, diluents, adjuvants, stabilizers, emulsifiers, preservatives, colorants, buffers, flavor-imparting agents, bacteriostatic agents, fungistatic agents, emollients, plasticizers, permeation enhancers, antioxidants, pigments, lubricants, preservatives, wetting agents, salts, and any mixture thereof, and pharmaceutically acceptable carriers suitable for oral, mucosal, submucosal, enteral, parenteral, intravenous or transdermal administration.

The disclosed pharmaceutical compositions may further comprise one or more of a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

The pharmaceutical compositions provided herein, when administered to a subject, may treat, control, manage or prevent diseases associated with uncontrolled inflammatory response such as, but not limited to, systemic juvenile idiopathic arthritis, Still's disease, Sjögren's syndrome and cancer. The subject may be an animal or a human subject.

Diagnosis with Machine Learning Classifier

The disclosed methods may comprise the use of a machine learning classifier to determine whether a subject is a good candidate for treatment. Machine learning classifiers include, but are not limited to, a random forest classifier.

The disclosed method may comprise collecting a biological sample from a subject; performing high-throughput RNA sequencing, such as Illumina sequencing, on the sample to sequence the RNA transcripts present in the cells of the sample; and matching at least some of the RNA reads output obtained from the high-throughput sequencing to their corresponding RNA transcripts in an RNA transcript dictionary.

The disclosed method may further comprise classifying some RNA reads that do not match an RNA transcript in the RNA transcript dictionary into a gene or gene family by one or more machine learning classifiers, such as neural networks, which have been trained to classify RNA reads to a gene or gene transcript based on training examples.

Further steps in the disclosed method may include quantifying the RNA transcripts. A first plurality of RNA reads that matched to an RNA transcript may be quantified by matching to RNA scaffolds that may be partially filled in according to matches with RNA reads and counted. A second plurality of RNA reads that were classified by the one or more machine learning classifiers may be quantified by assembling the RNA reads together by identifying RNA reads that map to the same gene or gene family and have overlapping sequence on an end. The assembled RNA transcripts may be counted. As a result an RNA transcriptome may be determined including the identity and quantity of RNA transcripts of the subject in the sample.

The RNA transcriptome may be input to a disease prediction machine learning classifier, such as a random forest classifier, that is trained to predict whether a subject has a disease or will have variation in treatment response. Variation in treatment response may include a subject reacting poorly to a standard treatment for a disease either by having an incomplete response to therapy or by causing new disease features to emerge. The disease prediction machine learning classifier may predict based on the RNA transcriptome whether the subject has elevated activity of TRIM8 and should be treated to disrupt or reduce TRIM8 activity as described herein.

The disclosed method may include administering treatment to the subject based on the output prediction of the disease prediction machine learning classifier.

The disclosed method may include, when the disease prediction machine learning classifier detects elevated activity of TRIM8, administering an effective dose of a pharmaceutical composition to inhibit TRIM8 activity and, when the disease prediction machine learning classifier does not detect elevated activity of TRIM8, not administering the effective dose. Further details of this method of diagnosis are described in U.S. Provisional Patent Application No. 62/719,614, filed on Aug. 18, 2018, which is hereby incorporated by reference in its entirety.

EXAMPLES

Example 1: Involvement of TRIM8 in Systemic Juvenile Idiopathic Arthritis (SJIA)

Clinical data were collected from 10 pediatric human subjects with SJIA and 10 healthy pediatric human subjects without SJIA (data not shown). Clinical data included sex, age at the time the blood sample was taken, symptoms, such as fever, rush, arthritis, hepatosplenomegaly, and lymphoadenopathy, white blood cell count, platelet count, erythrocyte sedimentation rate, C-reactive protein, TRIM8 content, ferritin content, soluble IL-2 receptor content, and type of SJIA medication taken.

Figure 7:
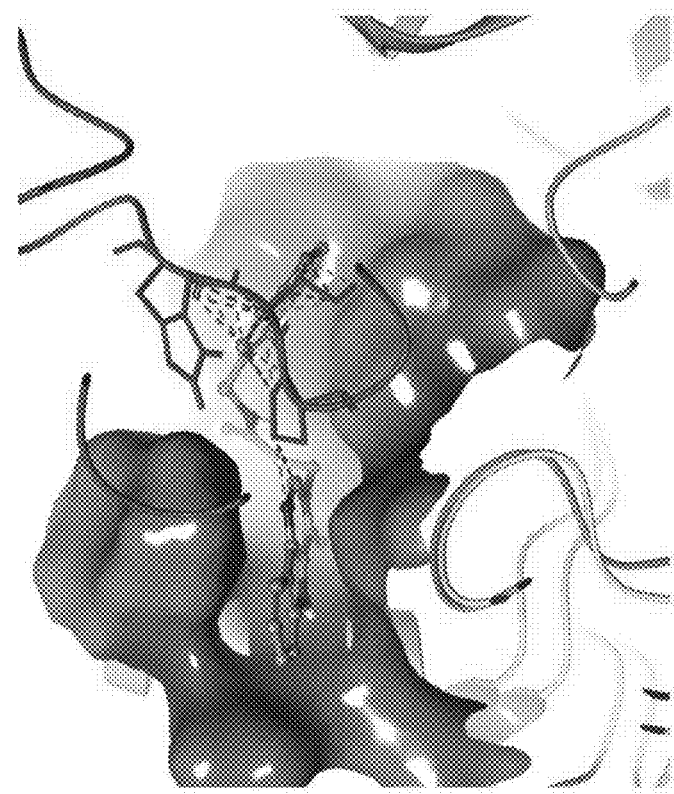
FIG. 7 provides a model showing the interaction between the E2-RING binding site of TRIM8 and small molecule compounds having a tricyclic region linked to a ring region connected to side chains that bind the E2-RING binding site of TRIM8. The model shows that the compounds used in the disclosed method form hydrogen bonds with Tyr 59 and hydrophobic bonds with Ile17 on the E2-RING.
Figure 7:
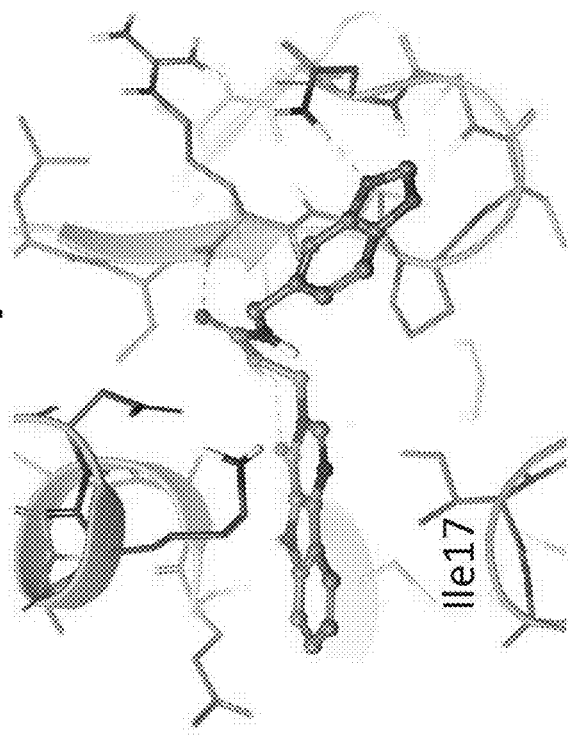
Figure 8:
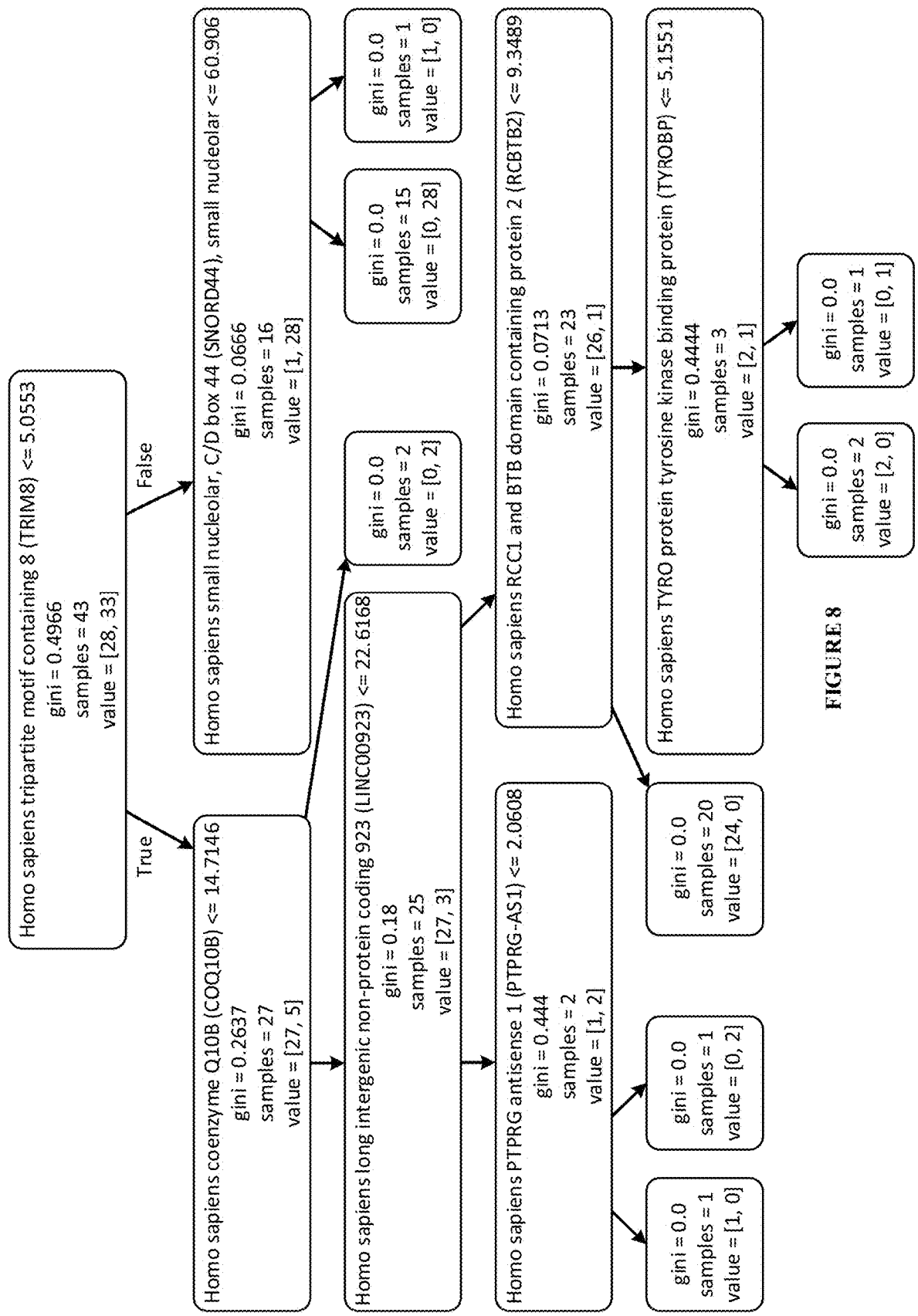
FIG. 8 shows a random forest analysis of all RNA transcripts detected in blood monocytes of pediatric subjects with and without Systemic Juvenile Idiopathic Arthritis (SJIA). The Random Forest was trained on disease (1) versus healthy control children (0).

In both groups, the age of the subjects ranged from 2 to 22. Blood monocytes were collected from each subject, cDNAs were isolated and RNA transcripts were prepared as described in the art. A Random Forest analysis was run on all RNA transcripts detected in the blood monocytes in each subject of each group to identify the factors responsible for the development of Macrophage Activation Syndrome (MAS), a life-threatening systemic inflammatory attack on the body. The Random Forest analysis, which was trained on disease (1) versus healthy control children (0), identified TRIM8 as a major factor in the development of MAS (see FIG. 7).

Example 2: Identification of Target Domains in TRIM8 and Small Molecule Inhibitors of TRIM8 Target Domains for Treatment of SJIA Computational models of the TRIM8 molecule were developed, and two regions on the TRIM8 protein were identified as suitable targets for the binding of small molecule inhibitors in order to disrupt or reduce TRIM8 activity: an E2-RING binding site and a RING-RING dimerization binding site (see FIGS. 1-6). Based on these findings, two different strategies to inactivate the TRIM8 protein were developed.

TRIM8 is a member of the tripartite motif protein family, an E3 ubiquitin-protein ligase family. E3 ubiquitin-protein ligases are known to regulate protein stability and protein degradation. Therefore, in a first strategy, the aim was to block the assembly of TRIM8 into its macromolecular complex including the E2 ligase, to prevent the degradation of proteins that are targeted by TRIM8, such as Suppressor Of Cytokine Signaling 1 (SOCS1), Protein Inhibitor Of Activated STAT 3 (PIAS3) and Transforming growth factor beta-activated kinase 1 (TAK1, also known as REF). The activities of these proteins are mediated by multiple cytokine signaling pathways, such as IL-1, IL-6 and TNF receptors, which in turn activate the IFN-I pathway. To this end, small molecule compounds were identified that bind the E2-RING binding site and prevent TRIM8 interaction with its targeted proteins. These small molecule inhibitors binding the E2-RING binding site of TRIM8 are characterized by the presence of a tricyclic region linked to a ring region connected to side chains. See E2 Top Examples.

In a second approach, the aim was to prevent TRIM8 homodimerization, a process that activates TRIM8, by targeting the RING-RING domain of TRIM8 with small molecule inhibitors, and thus destabilize and degrade TRIM8. Small molecule inhibitors were therefore identified that bind the RING-RING domain of TRIM8 protein. These small molecule inhibitors comprise a region comprising a terminal 6-member ring linked to a 5-member ring linked via a flexible linker to a central 6-member aromatic ring motif, which in turn is linked to another terminal 6-member ring. See Dimer-site examples.

Example 3: Screening of Small Molecule Compounds Comprising an E2-RING Domain or a RING-RING Domain as Inhibitors of TRIM8

A library of small molecule compounds comprising an E2-RING domain or a RING-RING domain was screen for TRIM8 inhibition in a cell-based assay. 20,000 THP-1 cells (a human myeloid cell line which imitates human monocyte cell inflammatory behavior and responds to IFN-γ stimulation by expressing interferon-γ family members CXCL9, CXCL10 and CXCL11) were incubated with 10 M of each compound (dissolved in DMSO) for 4 hours, then stimulated with 200 U (units) of human IFN-γ. The effect of the stimulation as measured by changes in accumulation levels of the cytokines CXCL9, CXCL10 and CXCL11 in extracellular fluid was determined by flow cytometer after 12 hours and compared to control (IFN-γ stimulation with no compound).

Table 1 below shows the degree of inhibition in inflammatory response, as measured by CXCL9, CXCL10 and CXCL11 expression following stimulation by IFN-γ, that was obtained from each compound that was selected after testing. Each compound is identified by its ChemDiv catalog number.

Values in Table 1 are reported as degree of change from the control state. Values less than 1 indicate inhibition of cytokine response, and values greater than 1 indicate enhancement of cytokine response. Smaller values indicate a higher degree of inhibition. Values closer to zero indicate profound inhibition of cytokine response, and thus significant suppression of inflammatory responses conferred via inhibition of TRIM8 by the tested compounds. CXCL11 values are higher due to a high background in their read-out (relatively high CXCL11 values indicate a high degree of inhibition). Standard errors reflect the degree of variation seen in the triplicate tests for each compound.

The molecules F616, E710, E950 and P759 conferred significant inhibition of inflammatory response. The molecules 3448 and V007 conferred significant enhancement of inflammatory response.

Based on these results, the inhibitors F616, E710, E950 and P759 and the enhancers 3448 and V007 were selected for further development.

The compound was synthesized as follows:

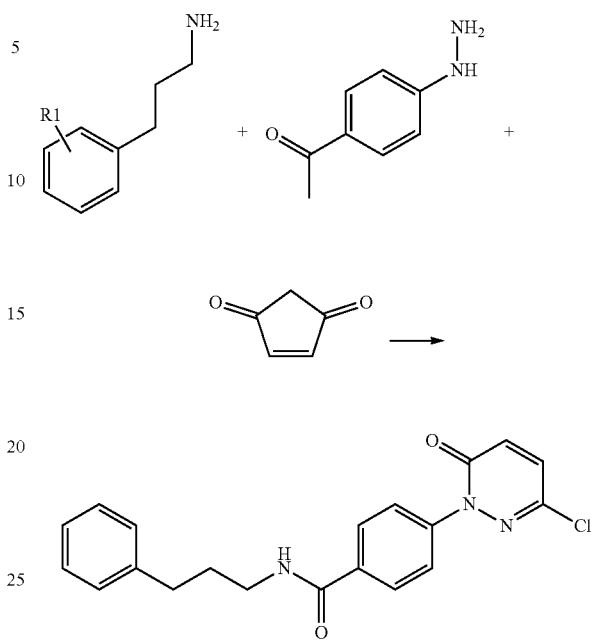

TABLE 1

| Compound | ChemDiv Compound Identifier | Normalized Average of MIG/CXCL9 | Normalized Average of IP-10/CXCL10 | Normalized Average of I-TAC/CXCL11 | Standard Error MIG/CXCL9 | Standard Error IP-10/CXCL10 | Standard Error I-TAC/CXCL11 | Average Normalized Cell Count |
|---|---|---|---|---|---|---|---|---|
| 88 | F616-0234 | 0.019 | 0.127 | 0.744 | 0.007 | 0.027 | . | 0.837 |
| 76 | E710-0005 | 0.085 | 0.352 | <LLOD | 0.006 | 0.030 | . | 1.196 |
| 81 | E950-0081 | 0.138 | 0.334 | 0.617 | 0.006 | 0.023 | . | 1.070 |
| 120 | P759-4354 | 0.188 | 0.468 | 0.426 | 0.042 | 0.052 | . | 0.960 |
| 130 | V007-0538 | 7.574 | 0.794 | 0.806 | 7.221 | 0.093 | 0.084 | 1.135 |
| 17 | 3448-1265 | 2.545 | 3.640 | 4.410 | 0.784 | 1.122 | 2.180 | 1.435 |

Example 4: Identification of TRIM8 Inhibitors and Enhancers

The compound 4-{3-[(4-methoxyphenyl)sulfanyl]-6-oxo-1,6-dihydropyridazin-1-yl}-N-(3-phenylpropyl)benzamide, is designated F616-0234, and it is represented by the formula:

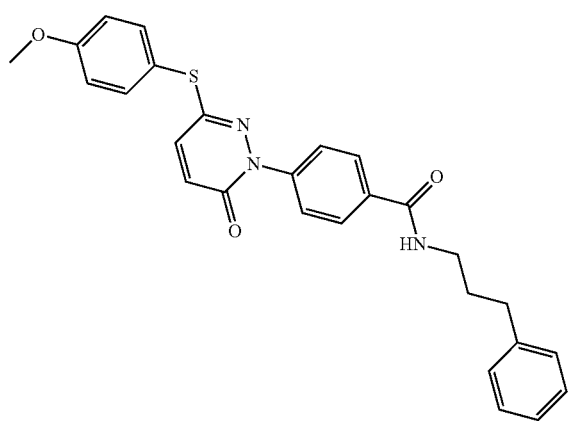 [SMILES: COc1ccc(Sc2ccc(=O)n(-c3ccc(C(=O)NCCCc4ccccc4)cc3)n2)cc1]

-continued

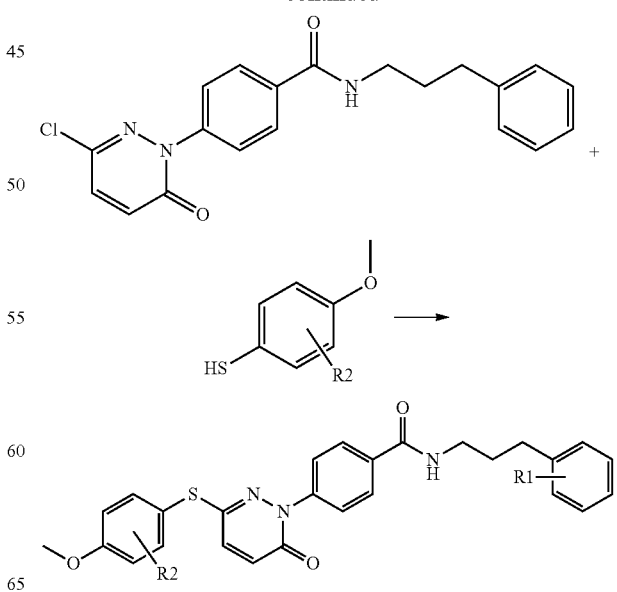

F616-0234 is a linear molecule with nearly C2 symmetry in its pharmacophore group as shown above. The particular length and pharmacophore C2 symmetry make the F616-0234 compound a highly potent TRIM8 inhibitor. This finding is supported by the fact that other TRIM8 inhibitors, such as the E950 compound, fit to opposite moieties of the F616-0234 structure.

The compound 5-(2,5-difluorobenzoyl)-N-(3-phenylpropyl)-1H,4H,5H,6H,7H-pyrazolo[4,3-c]pyridine-3-carboxamide, is designated P759-4354, and is represented by the formula

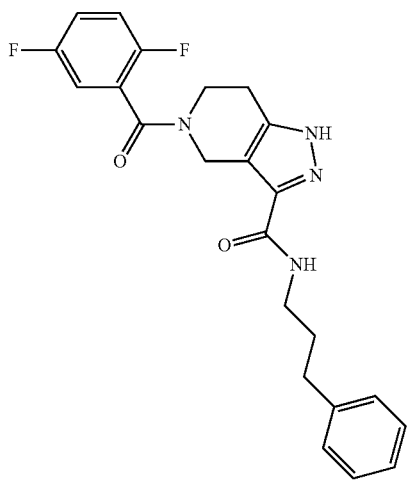 [SMILES: O=C(NCCCc1ccccc1)c1n[nH]c2c1CN(C(=O)c1cc(F)ccc1F)CC2]

The compound was synthesized as follows:

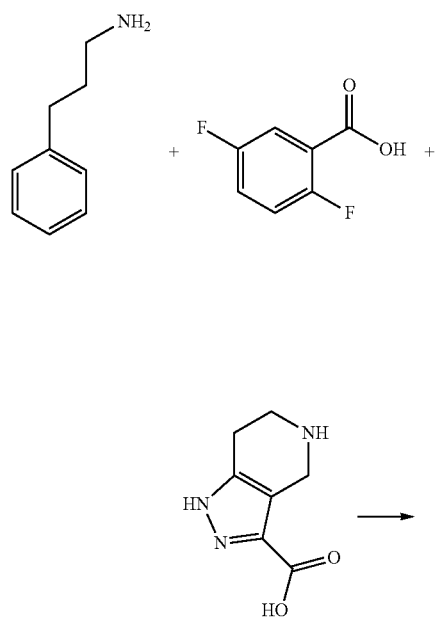

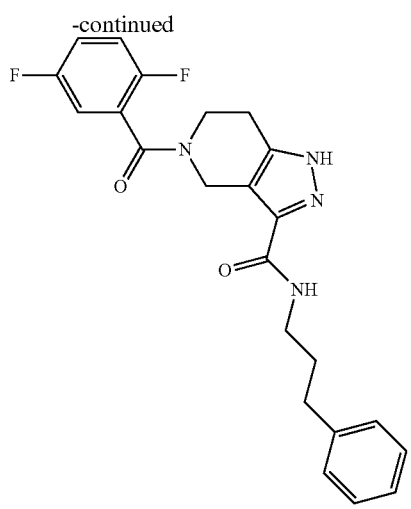

As the P759-4354 compound and the F616-0234 have identical aliphatic moieties, the P759-4354 compound was also found to be a TRIM8 inhibitor.

The compound 1-(4-methoxyphenyl)-4-{1H-pyrrolo[3,2-h]quinoline-2-carbonyl}piperazine is designated E950-0081 and is represented by the formula:

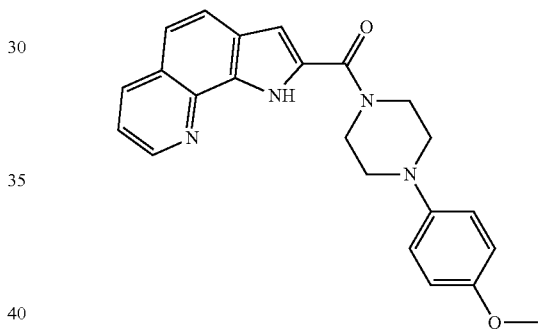

The compound was synthesized as follows:

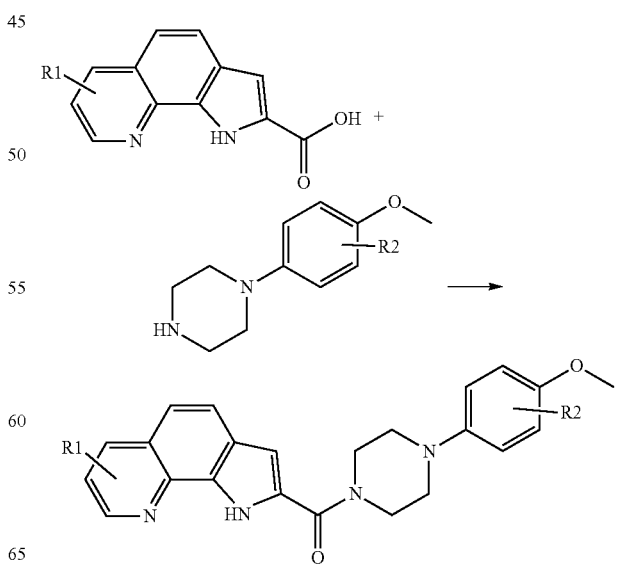

Testing revealed that the compound E950-0081 is a strong inhibitor of TRIM8. The compound is characterized by the presence of piperazines and heterocyclic moieties that fit in the structure of potent TRIM8 inhibitor F616-0234.

The compound 3-(4-methoxyphenyl)-7,7-dimethyl-4-phenyl-1H,4H,5H,6H,7H,8H,9H-pyrazolo[3,4-b]quinolin-5-one is designated E710-0005 and is represented by the formula:

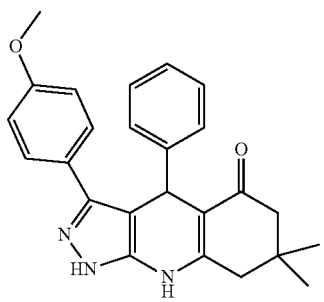 [SMILES: COc1ccc(-c2n[nH]c3c2C(c2ccccc2)C2=C(CC(C)(C)CC2=O)N3)cc1]

The compound was synthesized as follows:

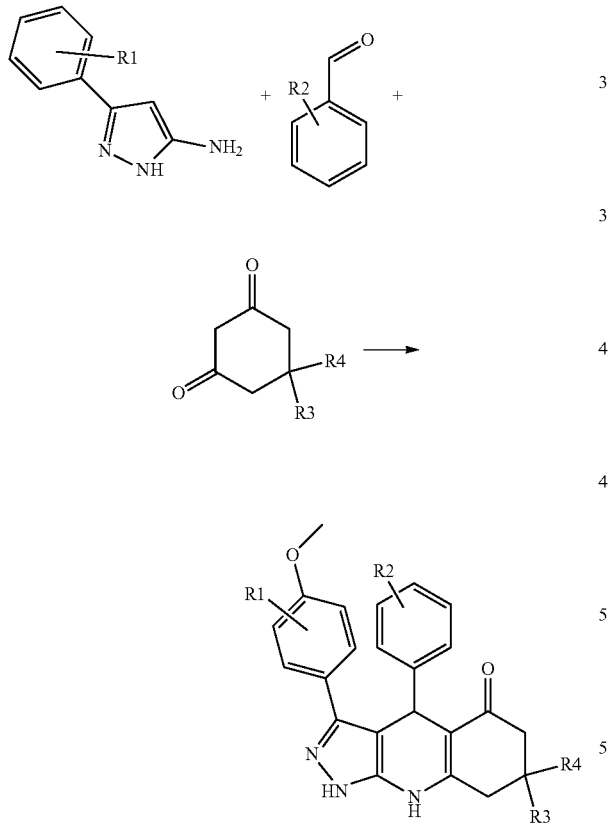

Testing of the compound E710-0005 revealed that the compound is a powerful TRIM8 inhibitor and its structure has a weak relationship to the structure of potent TRIM 8 inhibitor F616-0234.

The compound (5E)-1-[(4-methoxyphenyl)methyl]-5-[(naphthalen-1-yl)methylidene]-1,3-diazinane-2,4,6-trione is designated 3448-1265 and is represented by the formula

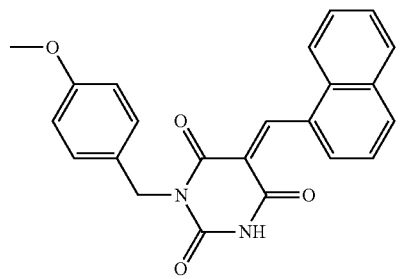 [SMILES: COc1ccc(CN2C(=O)NC(=O)/C(=C\c3cccc4ccccc34)C2=O)cc1]

The compound was synthesized as follows:

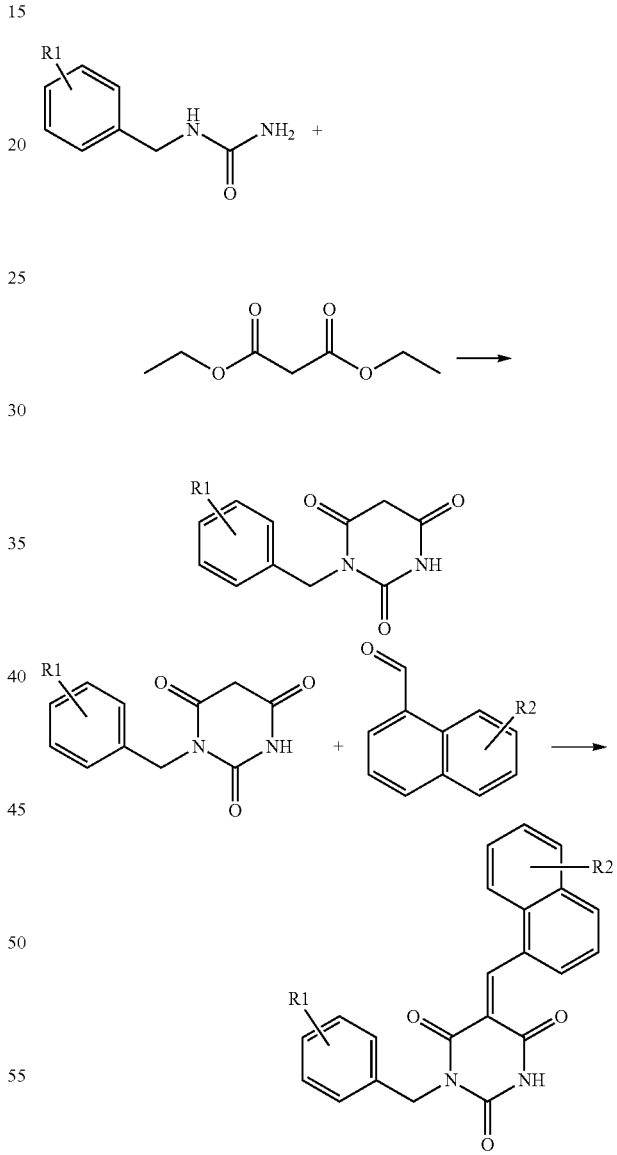

Testing of the 3448-1265 compound revealed that the compound is a potent TRIM8 enhancer, and that the 3448-1265 compound and the potent TRIM8 inhibitor F616-0234 have matching benzyl-heterocyclic moieties.

The compound 3-(2H-1,3-benzodioxol-4-yl)-3-(7-ethyl-1H-indol-3-yl)-1-[4-(4-nitrophenyl)piperazin-1-yl]propan-1-one is designated V007-0538 and is represented by the formula:

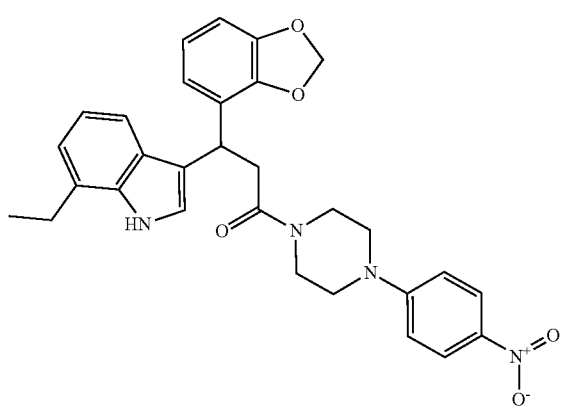 [SMILES: CCc1cccc2c(C(CC(=O)N3CCN(c4ccc([N+](=O)[O-])cc4)CC3)c3cccc4c3OCO4)c[nH]c12]

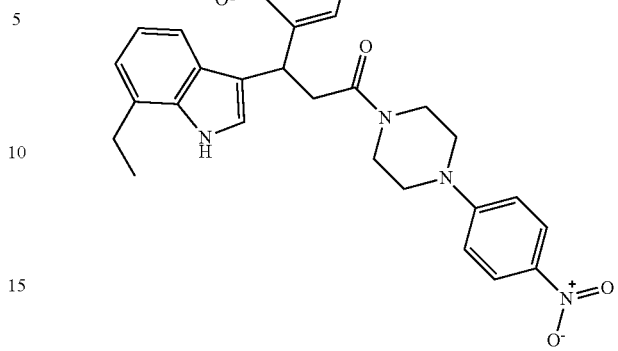

The compound was synthesized as follows:

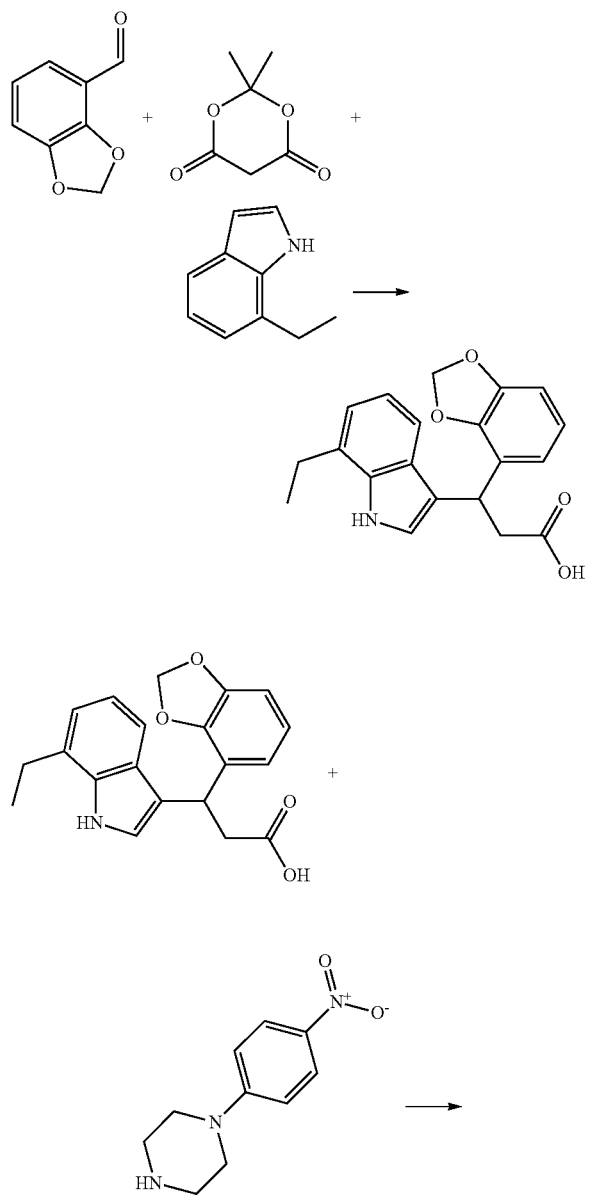

Testing of compound V007-0538 revealed that the compound is a potent TRIM8 enhancer characterized by the presence of a piperazine moiety that overlaps with the aliphatic moiety of potent TRIM8 inhibitor F616-0234, and an aromatic moiety, which only partially matches the aromatic moiety of F616-0234, leading to lack of interaction with the target.

Figure 11:
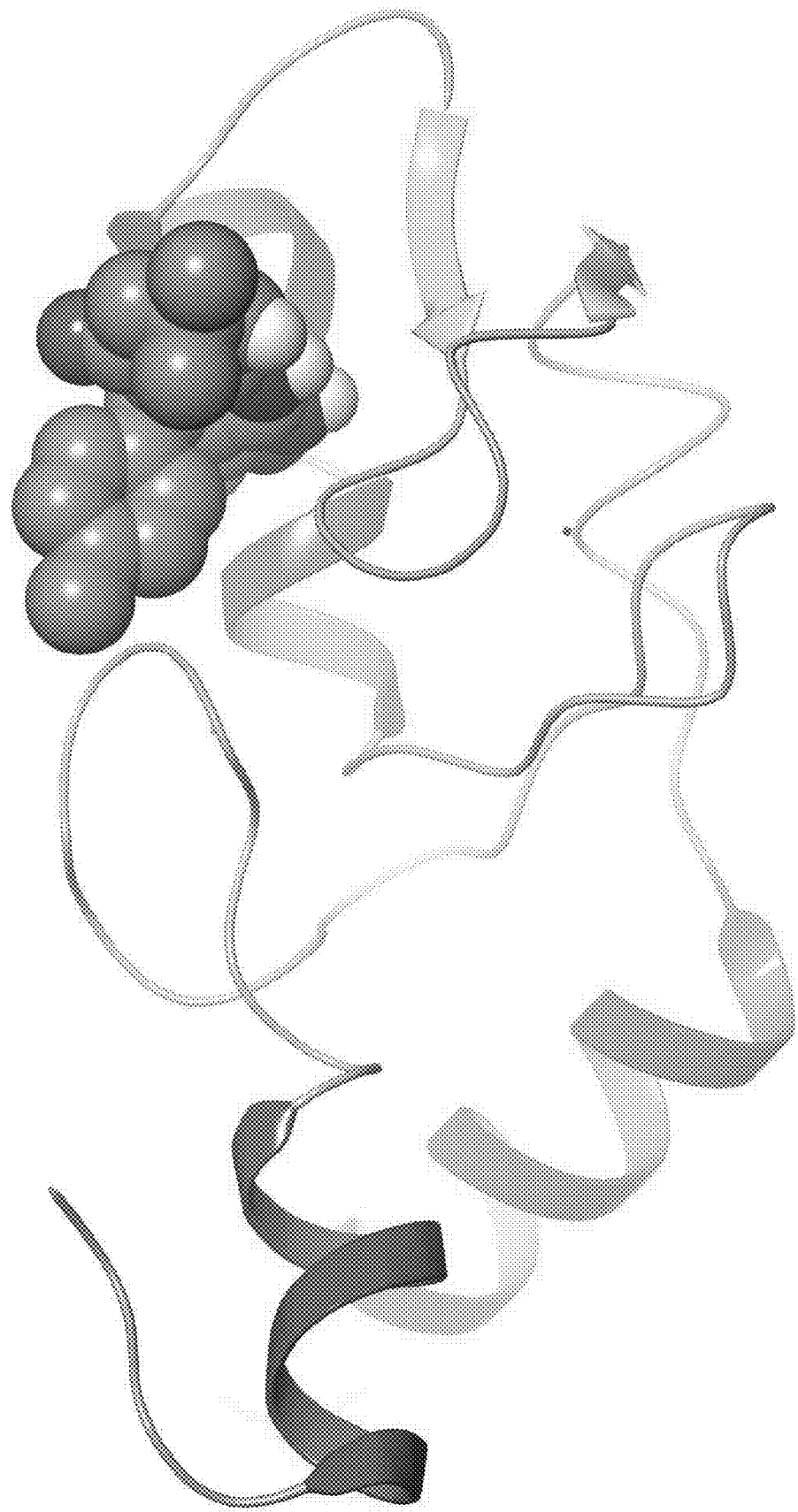
FIG. 11 is a model showing the binding of the E710 inhibitor to the TRIM8 protein via the E2 ubiquitin site. The contact residues at the interface are displayed as spheres.
Figure 12:
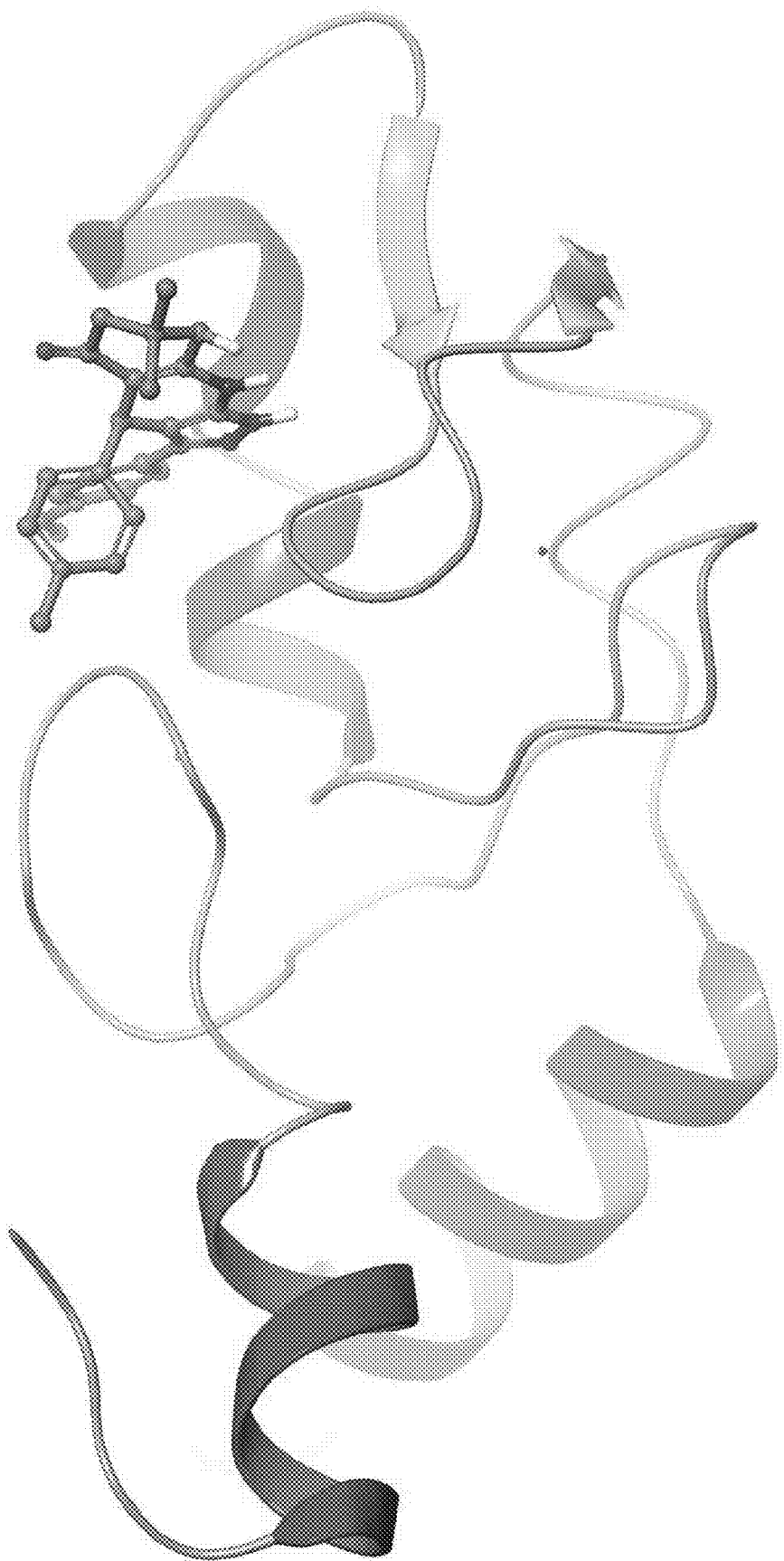
FIG. 12 is a model showing the binding of the E710 inhibitor to the TRIM8 protein via the E2 ubiquitin site. The contact residues at the interface are displayed as sticks.
Figure 13:
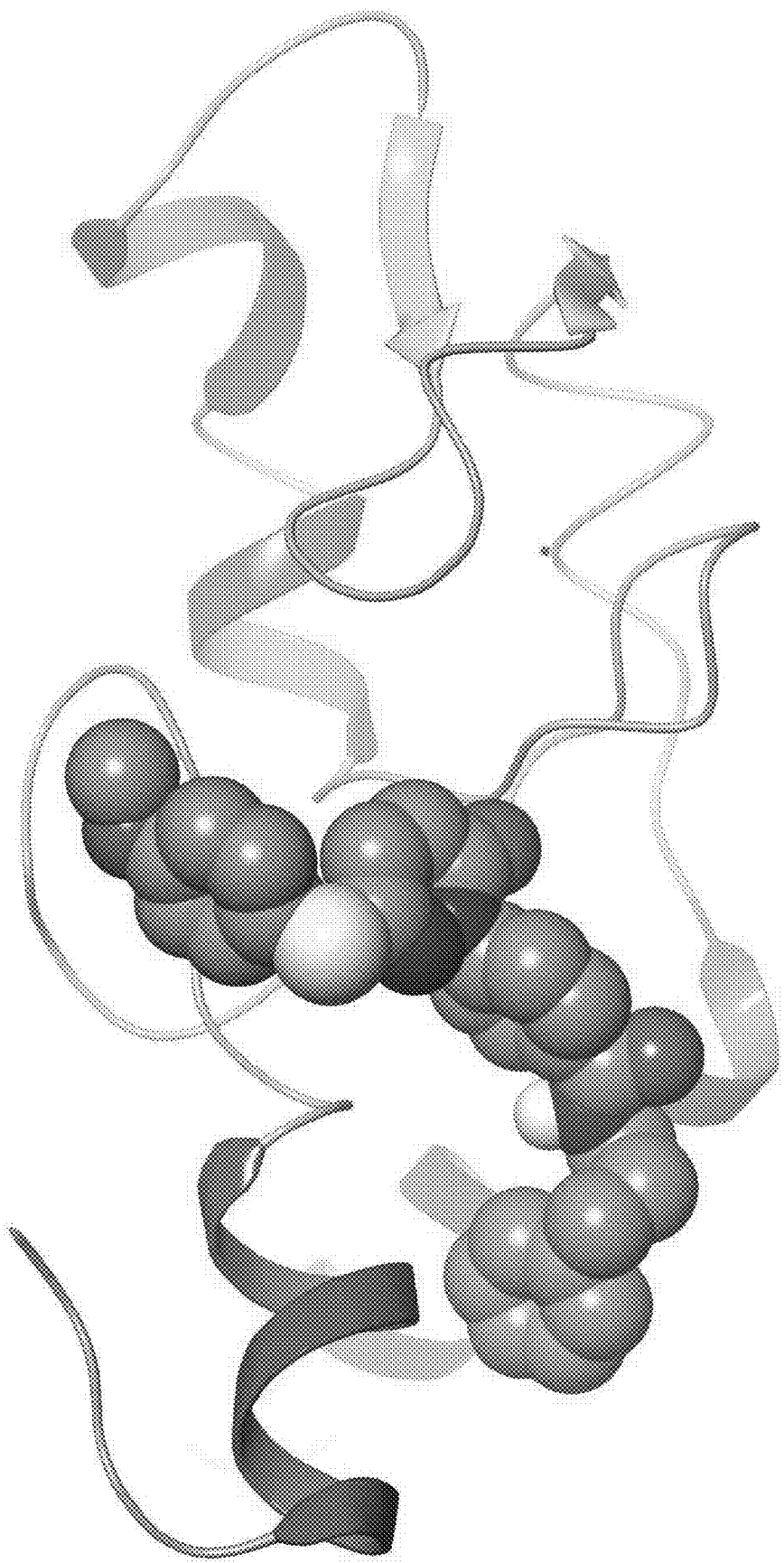
FIG. 13 is a model showing the binding of the F616 inhibitor to the TRIM8 protein via the dimerization site. The contact residues at the interface are displayed as spheres.
Figure 14:
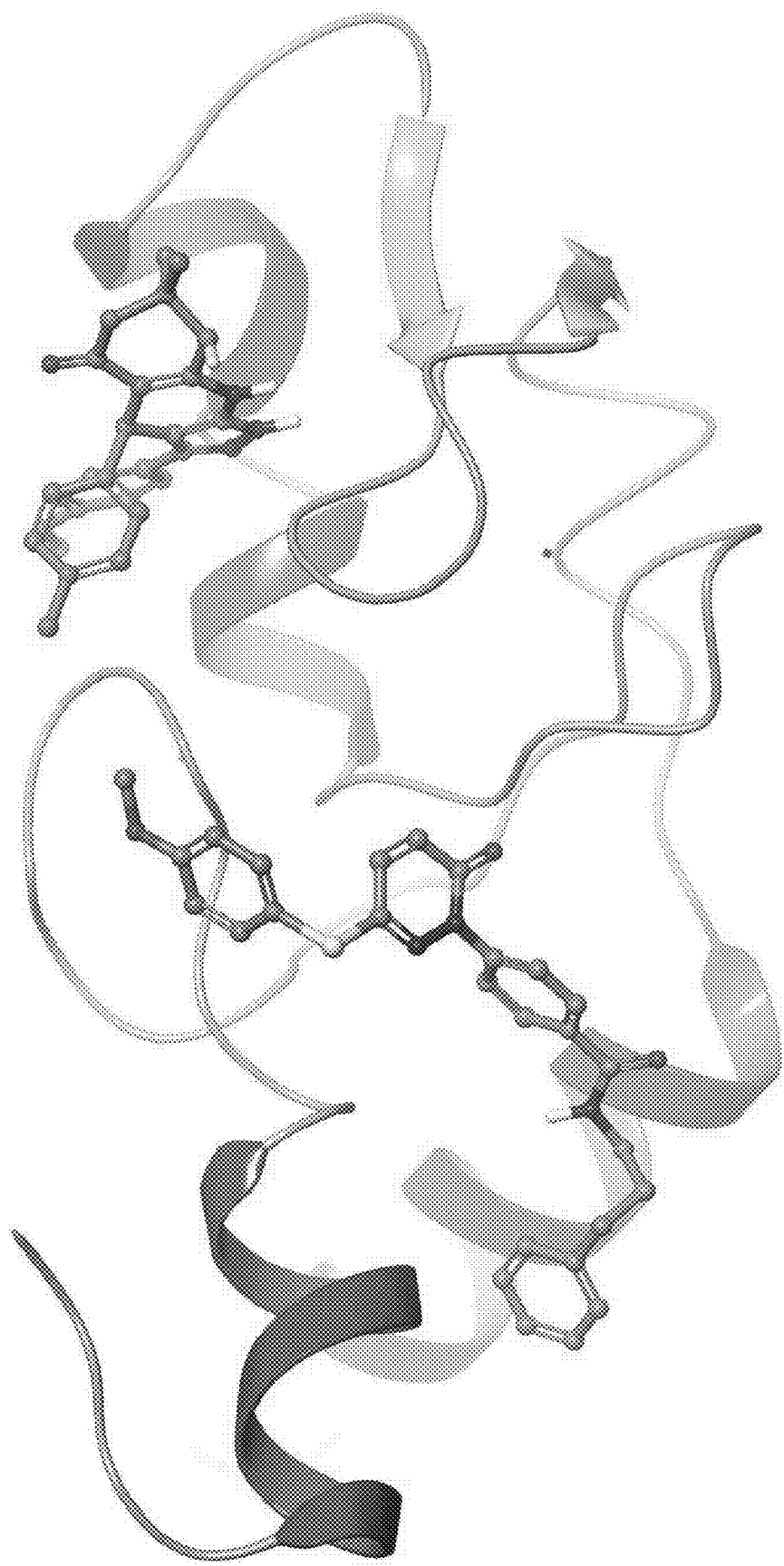
FIG. 14 is a model showing the binding of a small molecule to the TRIM8 protein via the dimerization site and the E2 ubiquitin site. The contact residues at the interface are displayed as sticks.
Figure 15:
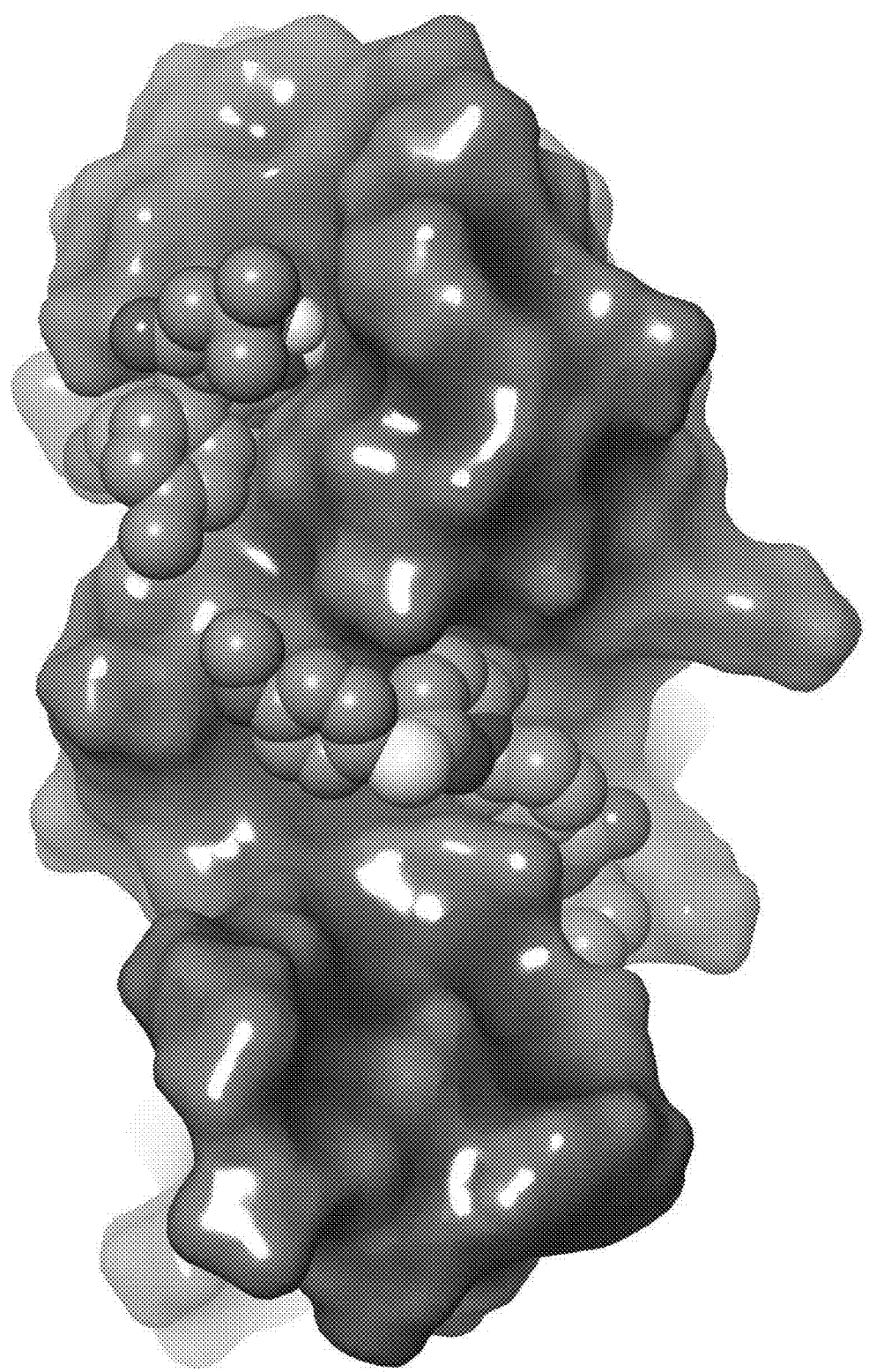
FIG. 15 is a model showing the binding of a small molecule to the TRIM8 protein via the dimerization site and the E2 ubiquitin site. The contact residues at the interface are displayed as spheres.
Figure 16:
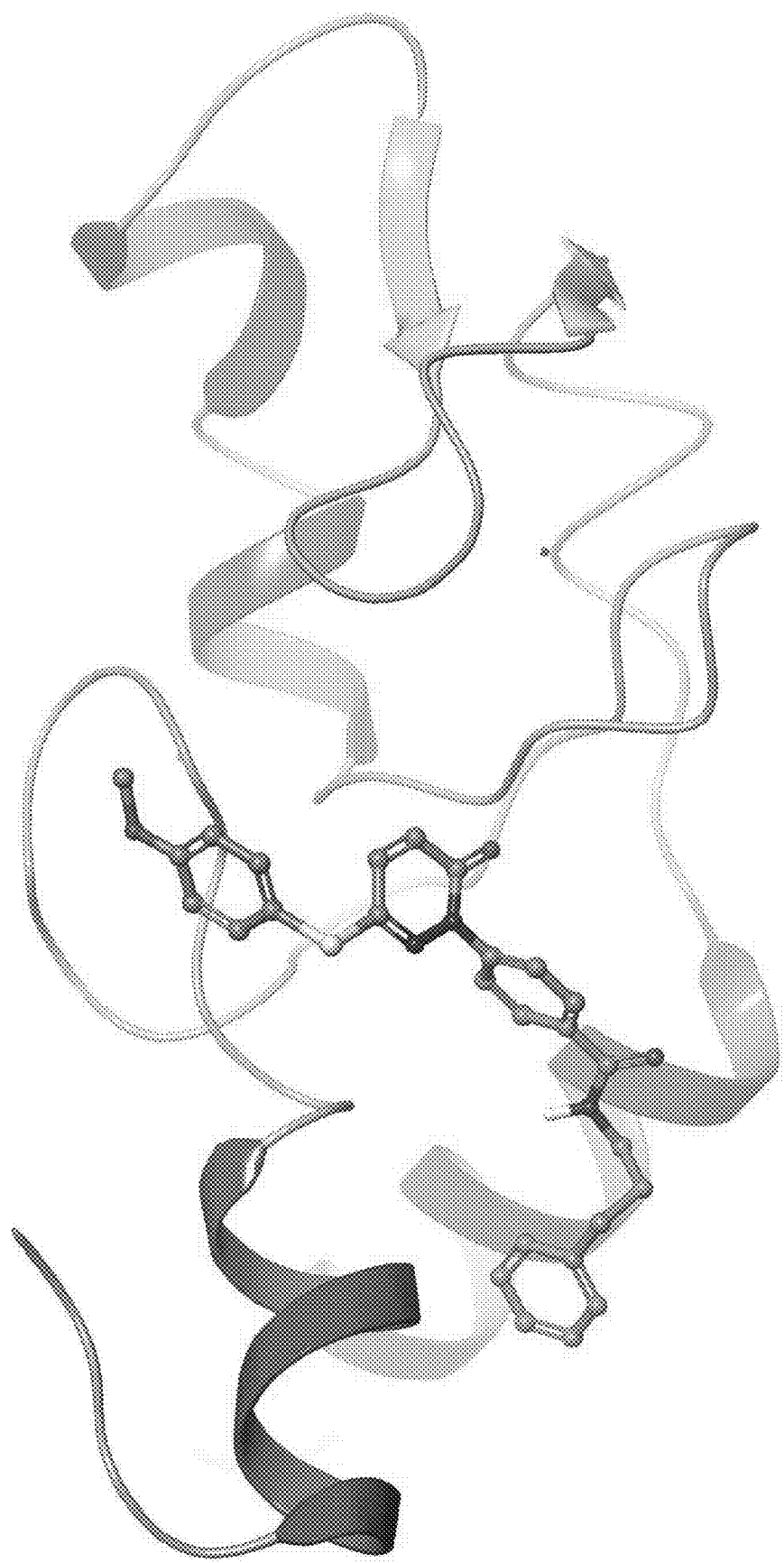
FIG. 16 is a model showing the binding of the F616 inhibitor to the TRIM8 protein via the dimerization site. The contact residues at the interface are displayed as sticks.
Figure 17:
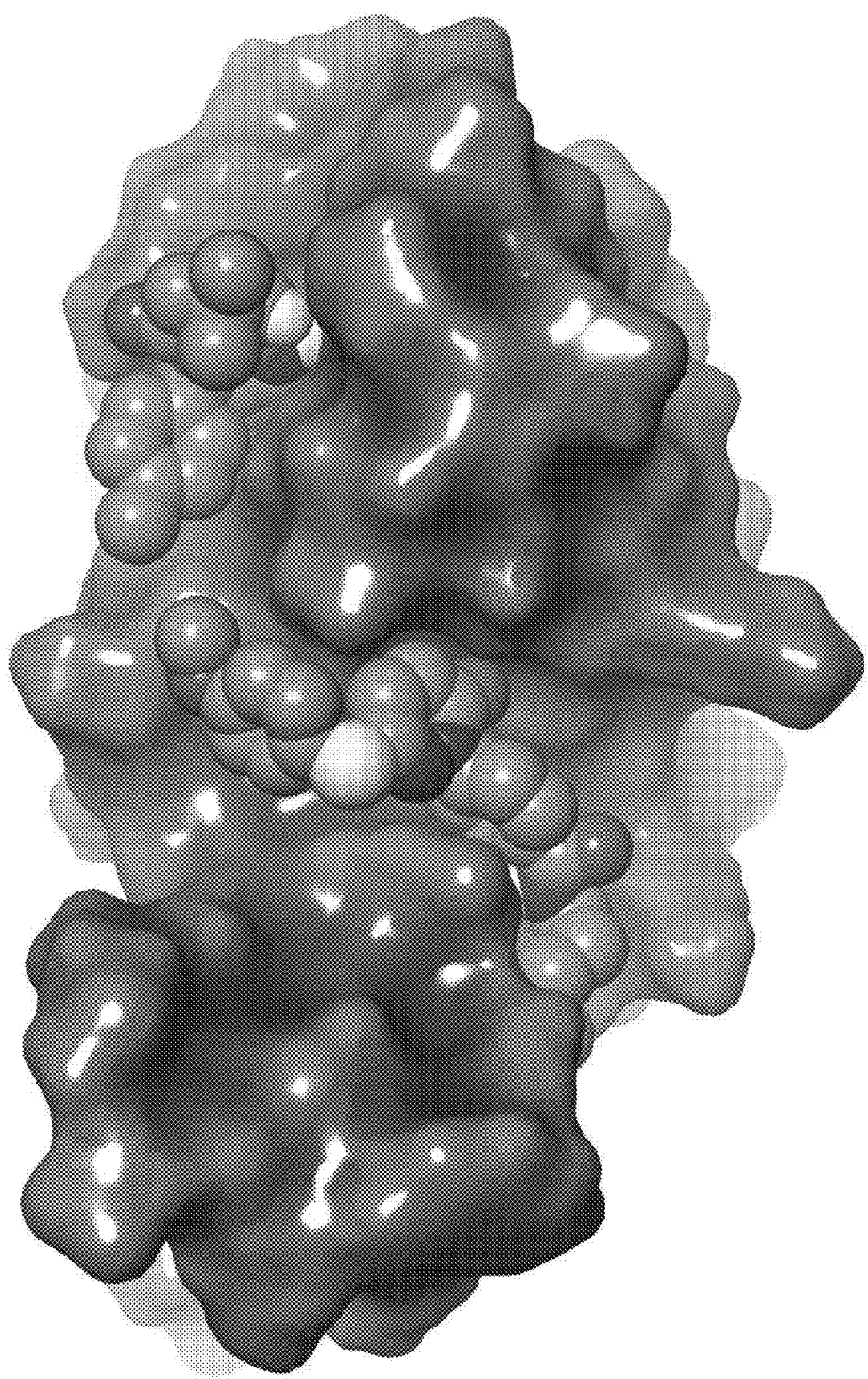
FIG. 17 is a model showing the binding of a small molecule to the TRIM8 protein via the dimerization site and the E2 ubiquitin site. The contact residues at the interface are displayed as spheres.
Figure 18:
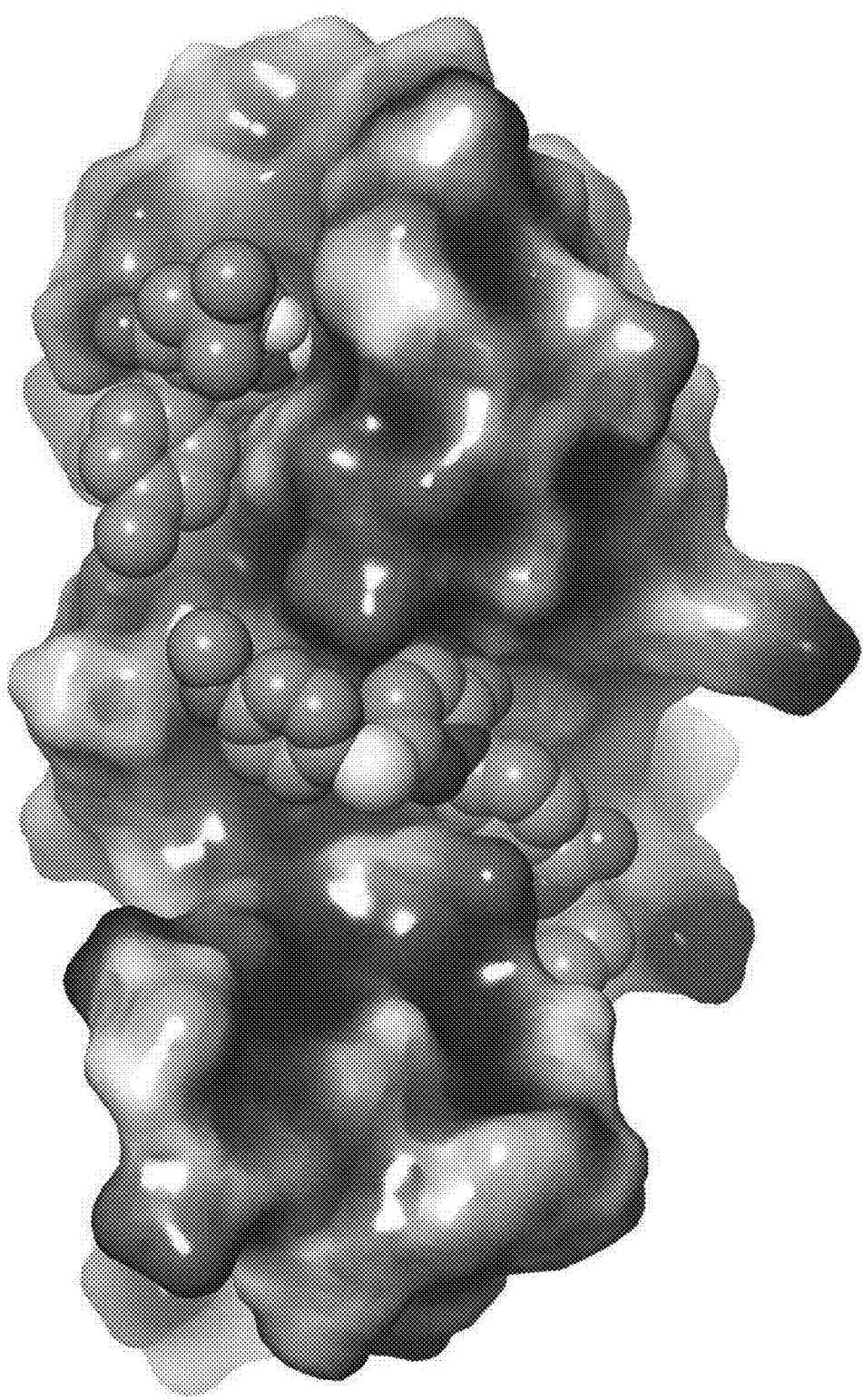
FIG. 18 is a model showing the binding of a small molecule to the TRIM8 protein via the dimerization site and the E2 ubiquitin site. The contact residues at the interface are displayed as spheres.
Figure 19:
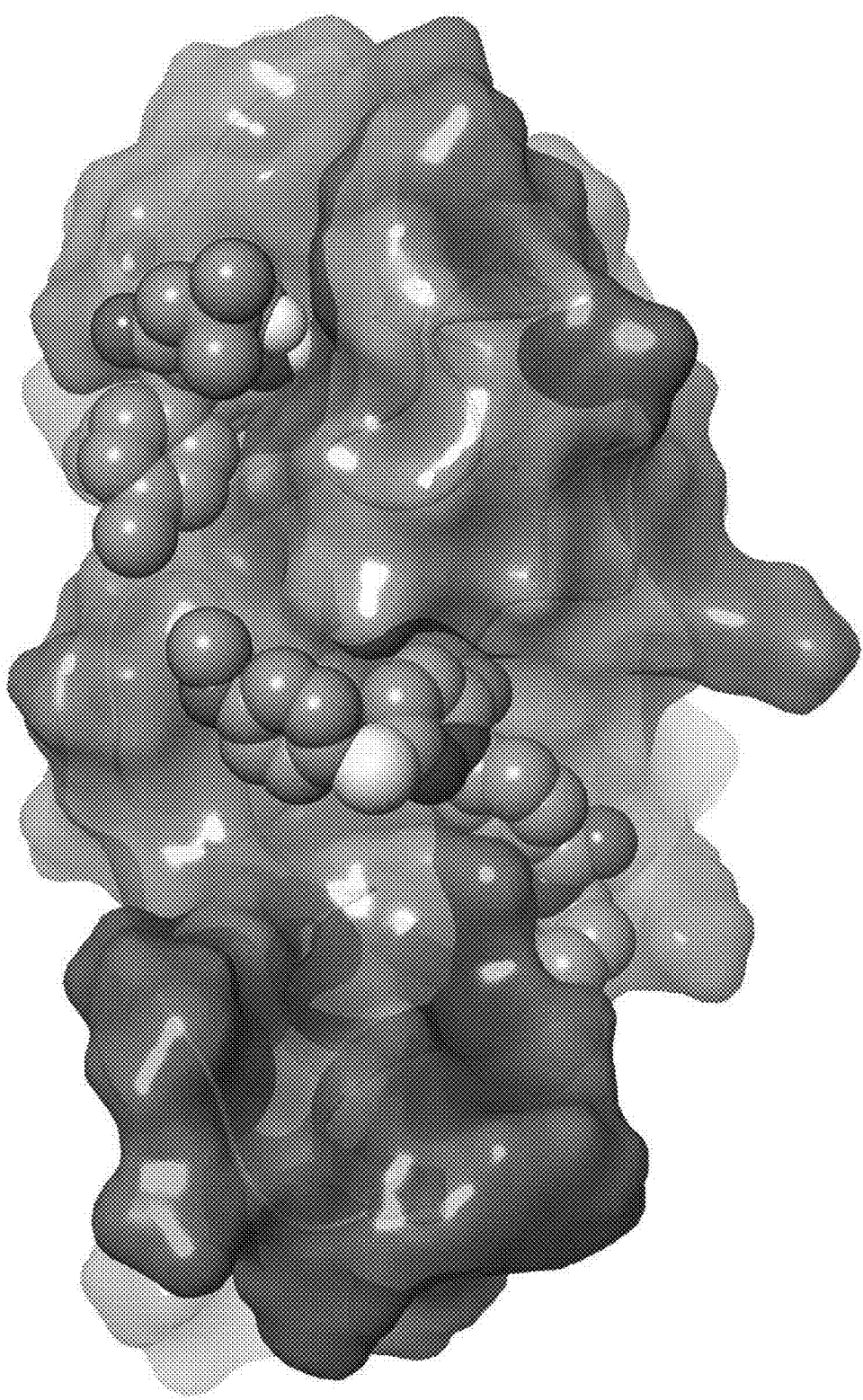
FIG. 19 is a model showing the binding of a small molecule to the TRIM8 protein via the dimerization site and the E2 ubiquitin site. The contact residues at the interface are displayed as spheres.
Figure 20:
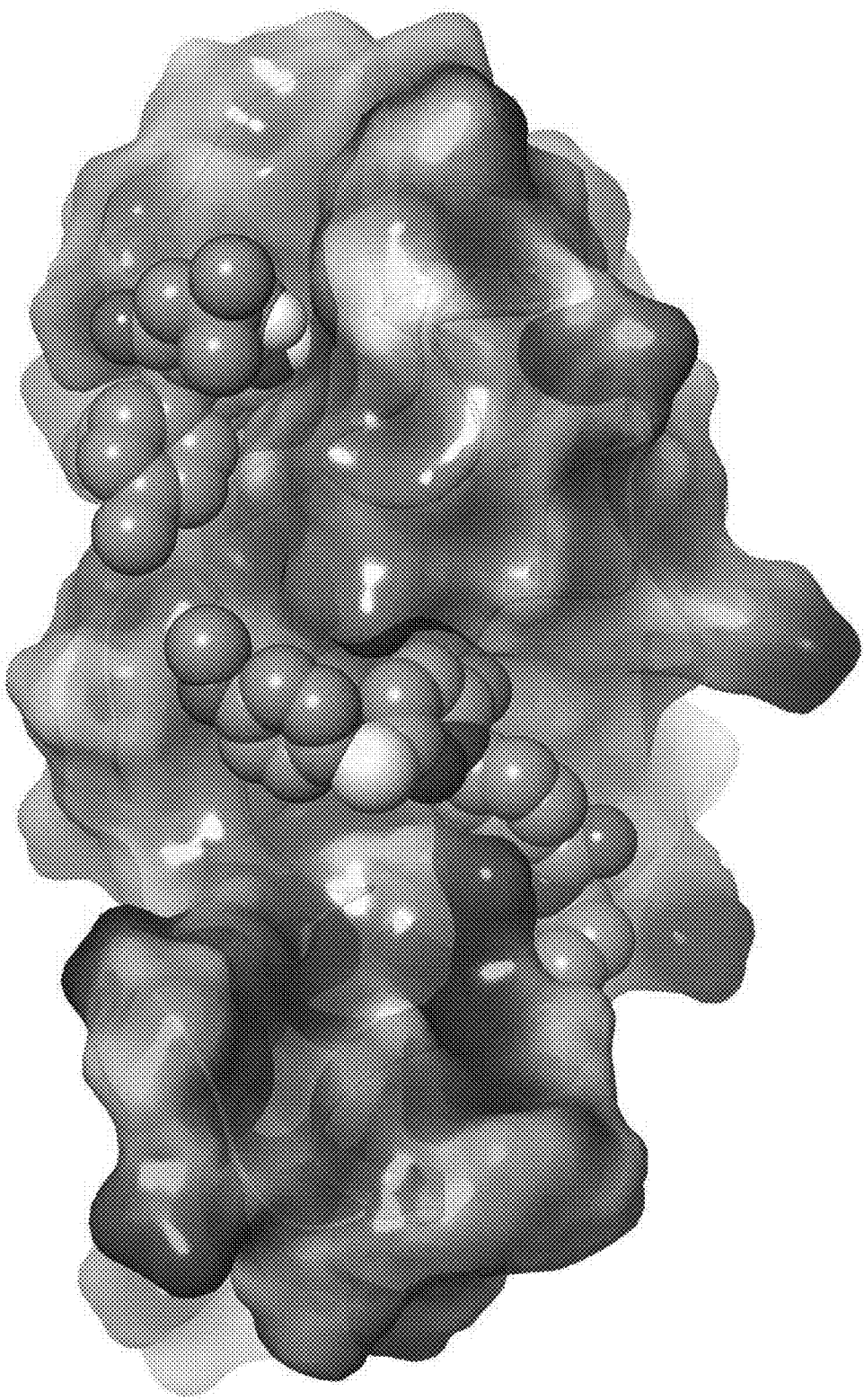
FIG. 20 is a model showing the binding of a small molecule to the TRIM8 protein via the dimerization site and the E2 ubiquitin site. The contact residues at the interface are displayed as spheres.

FIGS. 10-20 are models showing the binding of a small molecule to the TRIM8 protein via the dimerization site and/or the E2 ubiquitin site. The contact residues at the interface are displayed as spheres or sticks. In particular, FIGS. 11 and 12 show the binding of the E710 inhibitor to the TRIM8 protein via the E2 ubiquitin site. The contact residues at the interface are displayed as spheres and sticks, respectively. FIGS. 13 and 16 show the binding of the F616 inhibitor to the TRIM8 protein via the dimerization site. The contact residues at the interface are displayed as spheres and sticks, respectively.

These data indicate that TRIM8 potent inhibitor F616 targets the dimerization site of TRIM8, and disruption of the dimerization site in turn prevents degradation of SOCS1. Repression of the IFN-I pathway by SOCS1 blocks inflammation by CXCL9, CXCL10 and CXCL11. These data additionally indicate that TRIM8 inhibitor E710 targets the E2 ubiquitin site. Disruption of the E2 ubiquitin site prevents SOCS1 degradation, which blocks or reduces inflammation by CXCL9, CXCL10 and CXCL11.

Figure 9:
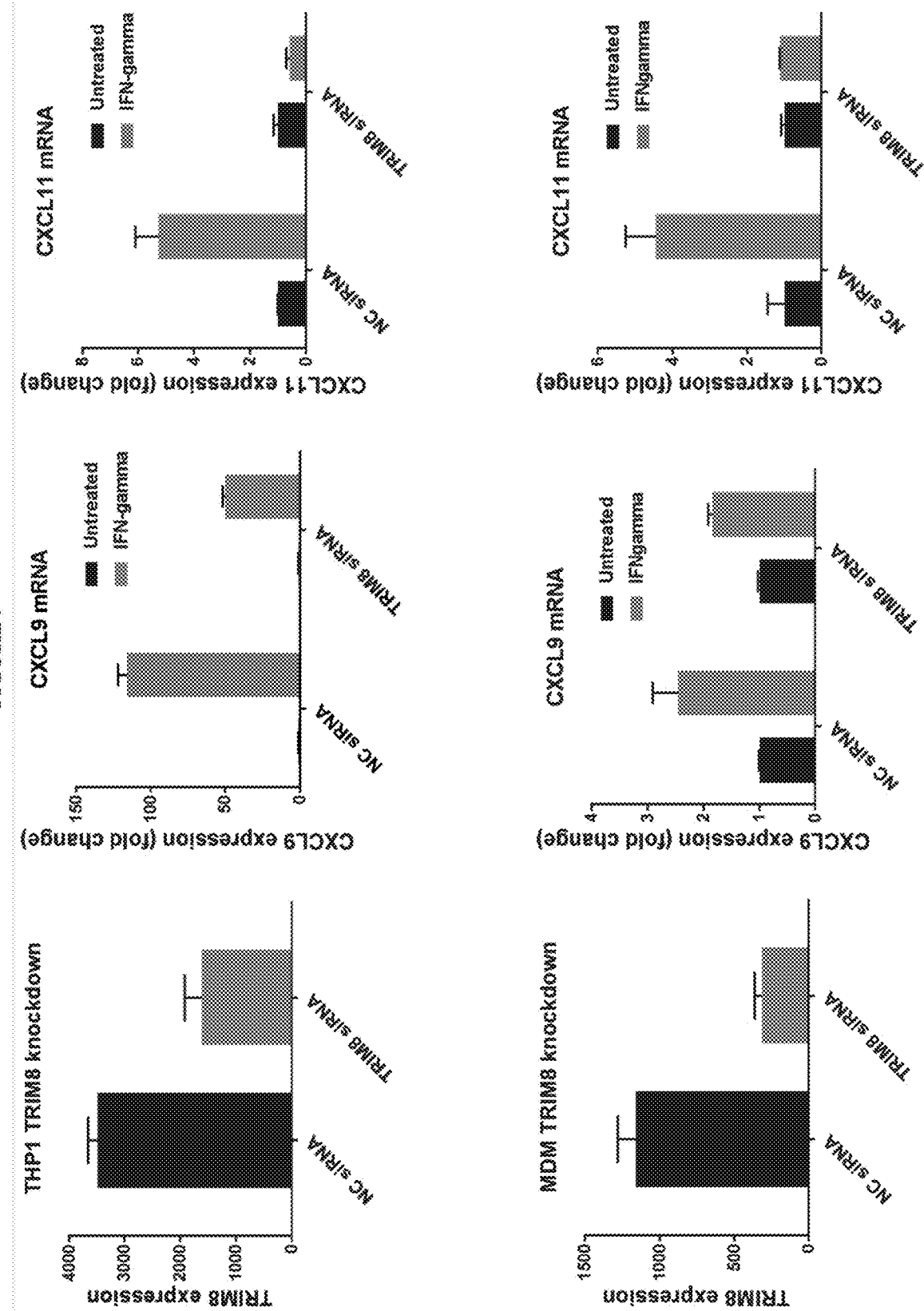
FIG. 9 shows the effect of TRIM8 expression silencing on cytokine stimulation through the IFN-I pathway. The results demonstrate that reduction of TRIM8 is sufficient to dramatically reduce cytokine responses through the IFN-I receptor pathway.
Figure 10:
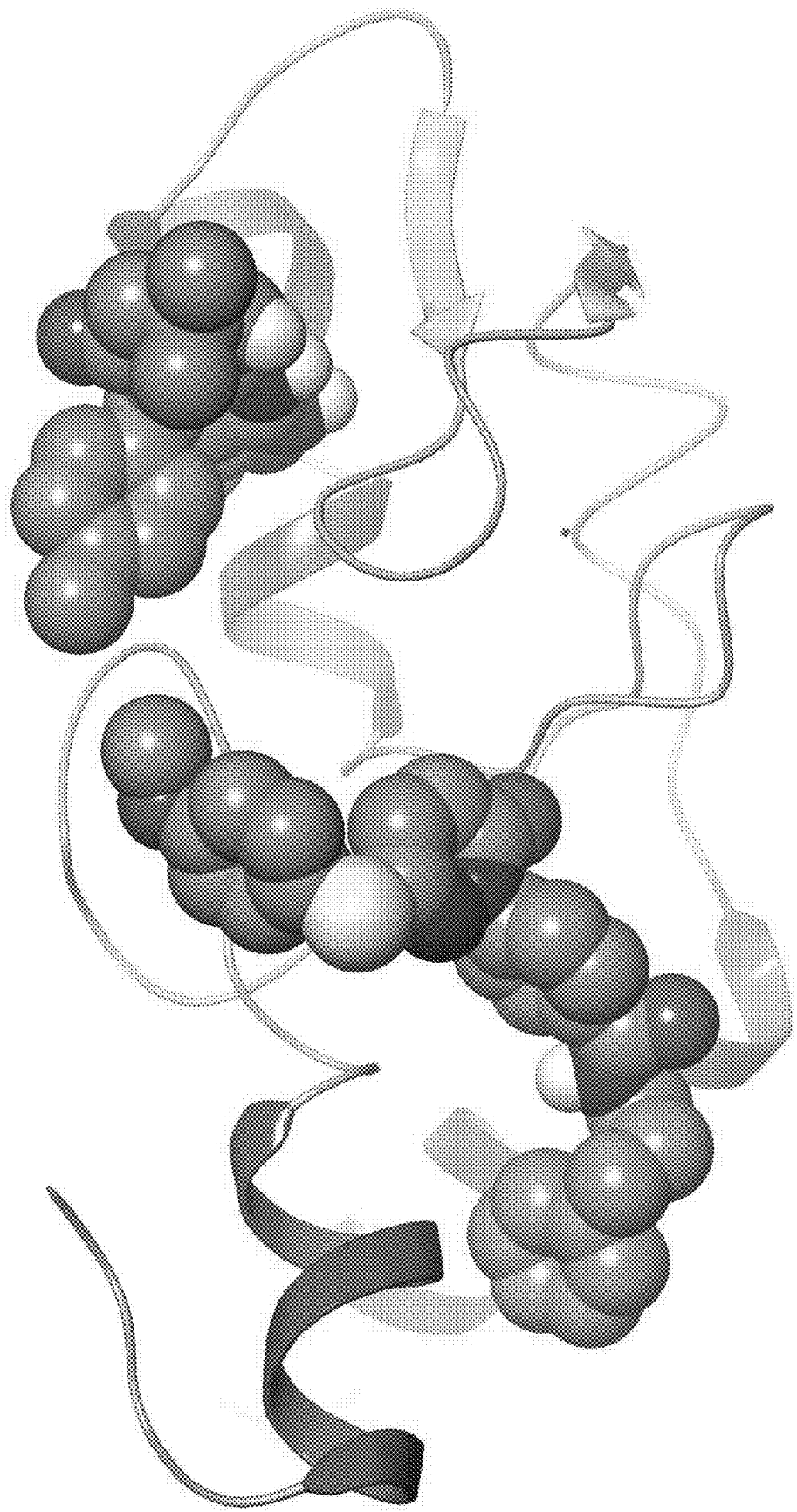
FIG. 10 is a model showing the binding of a small molecule to the TRIM8 protein via the dimerization site and the E2 ubiquitin site. The contact residues at the interface are displayed as spheres.

Example 5: Effect of TRIM8 Silencing on Cytokine Response Through the IFN-I Receptor Pathway In order to measure cytokine activity in inflammatory pathways controlled by TRIM8 and known to be active in SJIA, the expression of TRIM8 was reduced in ex vivo cell systems using interfering RNA system to bind to and degrade TRIM8 RNA transcripts. RNA expression of TRIM8 was reduced in THP-1 cells, a myeloid cell line having monocyte cell functions, and in patient blood monocytes, and the effect of the reduction in TRIM8 expression on the cytokines CXCL9 and CXCL11 was measured in the THP-1 cells and in the blood monocytes. Following reduction of TRIM8 expression, THP-1 and monocytes were stimulated with 200 U per ml of IFN-γ for 12 hours. At the end of treatment, a strong reduction was observed in the expression of CXCL9 and CXCL11 even after stimulation by IFN-γ (see FIG. 9). CXCL9, CXCL10 and CXCL11 cytokines are directly responsive to stimulation by IFN-γ via the IFN-I receptor found on the surface of all THP-1 cells and primary monocytes. These results demonstrate that reduction of TRIM8 is sufficient to dramatically reduce cytokine responses through the IFN-I receptor pathway.

Example 6: Efficacy of the Disclosed Pharmaceutical Composition in Patients with Moderate-to-Severe Sjögren's Syndrome The superiority of efficacy and safety of the disclosed pharmaceutical compositions compared to placebo is assessed for treatment of signs and symptoms in subjects with moderate-to-severe Sjögren's syndrome exhibiting one or more symptoms of systemic disease.

The disclosed pharmaceutical compositions comprising one or more small molecule inhibitors are administered i.v. in two initial doses at days 1 and 15. This experimental regimen is compared to a same regimen where a pharmaceutical composition containing placebo is administered in place of the disclosed small molecule inhibitors. 10 subjects are included in each of the two groups. Subjects are monitored for disease activity and symptoms, such as dryness, joint pain and fatigue, TRIM8 content in blood monocytes, abnormally elevated expression of one or more cytokines, one or more cytokine receptors, or one or more signaling pathway, over a period of one year.

At the end of the one year period, subjects treated with the disclosed pharmaceutical compositions show a significant improvement of symptoms and indicators of Sjögren's syndrome over the control.

It should be recognized that illustrated embodiments are only examples of the disclosed product and methods and should not be considered a limitation on the scope of the invention. Rather, the scope of the invention is defined by the following claims. We therefore claim as our invention all that comes within the scope and spirit of these claims.

The invention claimed is:

1. A method of treating, controlling or managing a disease associated with uncontrolled inflammatory response in a subject in need thereof, wherein the method comprises altering TRIM8 activity in the subject's blood monocytes by administering to the subject a pharmaceutical composition comprising a small molecule compound that targets TRIM8 E2-RING binding site or TRIM8 RING-RING dimerization binding site.

2. The method of claim 1, wherein the small molecule compound binds the E2-RING binding site of TRIM8 and wherein the small molecule inhibitor comprises a tricyclic region linked to a ring region connected to side chains.

3. The method of claim 2, wherein the small molecule compound comprises the formula.

4. The method of claim 2, wherein the small molecule compound comprises the formula:

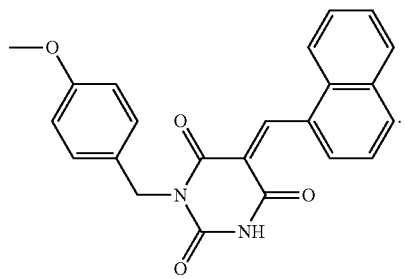 [SMILES: COc1ccc(CN2C(=O)NC(=O)/C(=C\c3cccc4ccccc34)C2=O)cc1]

5. The method of claim 2, wherein the small molecule compound comprises the formula:

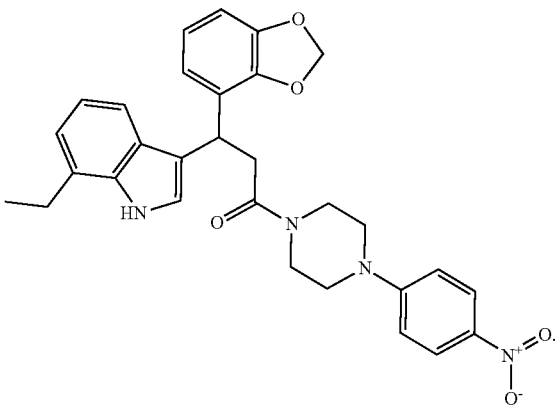 [SMILES: CCc1cccc2c(C(CC(=O)N3CCN(c4ccc([N+](=O)[O-])cc4)CC3)c3cccc4c3OCO4)c[nH]c12]

6. The method of claim 1, wherein the small molecule compound binds the RING-RING dimerization binding site of TRIM8, and wherein the small molecule compound comprises a region comprising a terminal 6-member ring linked to a 5-member ring linked via a flexible linker to a central 6-member aromatic ring motif, which in turn is linked to another terminal 6-member ring.

7. The method of claim 6, wherein the small molecule compound is a compound comprising the formula:

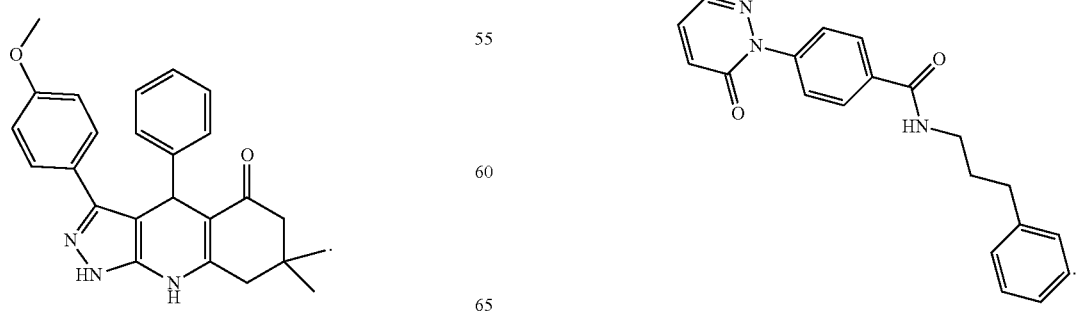

8. The method of claim 6, wherein the small molecule compound is a compound comprising the formula:

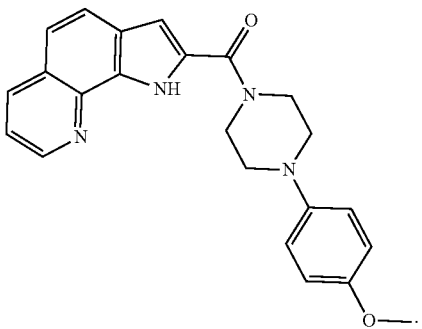 [SMILES: COc1ccc(N2CCN(C(=O)c3cc4ccc5cccnc5c4[nH]3)CC2)cc1]

9. The method of claim 6, wherein the small molecule compound is a compound comprising the formula:

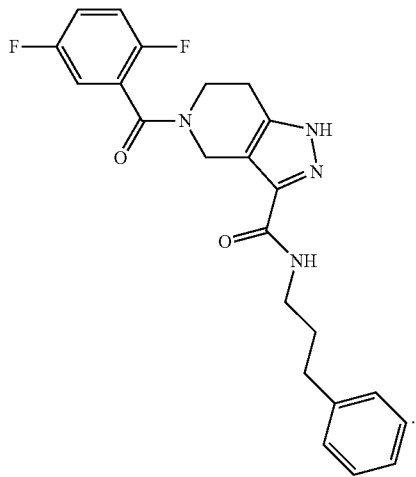 [SMILES: O=C(NCCCc1ccccc1)c1n[nH]c2c1CN(C(=O)c1cc(F)ccc1F)CC2]

10. The method of claim 1, wherein the pharmaceutical composition is formulated for oral, enteral, parenteral, intravenous, pulmonary, mucosal, sub-mucosal or transdermal administration.

11. The method of claim 10, wherein the pharmaceutical composition contains one or more pharmaceutically acceptable excipients, diluents, adjuvants, stabilizers, emulsifiers, preservatives, colorants, buffers, flavor-imparting agents or pharmaceutically acceptable carriers suitable for oral, enteral, mucosal, sub-mucosal, parenteral, intravenous or transdermal administration.

12. The method of claim 11, wherein the pharmaceutical composition further comprises one or more of a chemotherapeutic agent, an immunosuppressive agent, an immunostimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteoinductive factor, an antibacterial agent or an antifungal agent.

13. The method of claim 1, wherein the disease associated with uncontrolled inflammatory response is systemic juvenile idiopathic arthritis, Still's disease, Sjögren's syndrome or cancer.

14. The method of claim 1, wherein the method further comprises a step of identifying an uncontrolled inflammatory response in the subject prior to reducing abnormally elevated expression of TRIM8 in the subject's blood monocytes.

15. The method of claim 14, wherein the step of identifying an uncontrolled inflammatory response in the subject comprises detecting abnormally elevated expression of one or more cytokine, one or more cytokine receptor, one or more protein, or one or more signaling pathway in the subject.

16. The method of claim 15, wherein the cytokine is one or more of CXCL9, CXCL10, CXCL11, S100A8, S100A9, S100A12, IL-1 beta, IL-6 or TNF.

17. The method of claim 15, wherein the protein is TRIM8.

18. The method of claim 15, wherein the signaling pathway is one or more of suppressor of cytokine signaling-1 (SOCS1) pathway, Janus tyrosine Kinase (JAK) pathway, or Signal Transducer and Activator of Transcription (STAT) pathway.

19. The method of claim 1, further comprising detecting the abnormally elevated expression of TRIM8 in the subject's blood monocytes by reconstructing an RNA transcriptome from a list of RNA reads of the subject and inputting the RNA transcriptome into a machine learning classifier trained to detect the expression of TRIM8.

20. A pharmaceutical composition for prevention, management and/or treatment of a disease associated with uncontrolled inflammatory response, wherein the pharmaceutical composition comprises a small molecule compound that binds TRIM8 E2-RING binding site or TRIM8 RING-RING dimerization binding site.

21. The pharmaceutical composition of claim 20, wherein the small molecule compound binds the E2-RING binding site of TRIM8 and wherein the small molecule compound comprises a tricyclic region linked to a ring region connected to side chains.

22. The pharmaceutical composition of claim 21, wherein the small molecule compound comprises the formula:

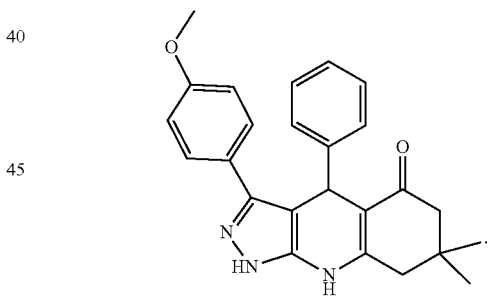

23. The pharmaceutical composition of claim 21, wherein the small molecule compound comprises the formula:

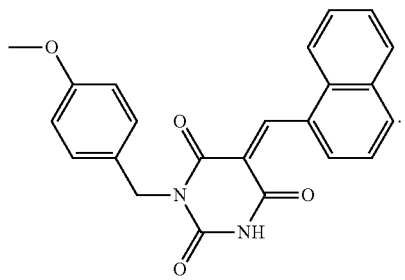 [SMILES: COc1ccc(CN2C(=O)NC(=O)/C(=C\c3cccc4ccccc34)C2=O)cc1]

24. The pharmaceutical composition of claim 21, wherein the small molecule compound comprises the formula:

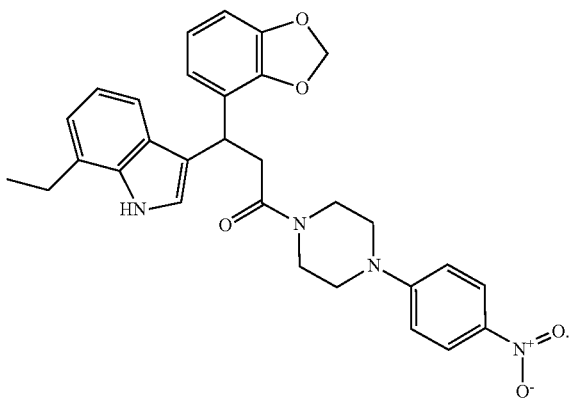 [SMILES: CCc1cccc2c(C(CC(=O)N3CCN(c4ccc([N+](=O)[O-])cc4)CC3)c3cccc4c3OCO4)c[nH]c12]

25. The pharmaceutical composition of claim 21, wherein the small molecule compound binds the RING-RING dimerization binding site of TRIM8, and wherein the small molecule compound comprises a region comprising a terminal 6-member ring linked to a 5-member ring linked via a flexible linker to a central 6-member aromatic ring motif, which in turn is linked to another terminal 6-member ring.

26. The pharmaceutical composition of claim 25, wherein the small molecule compound is a compound comprising the formula:

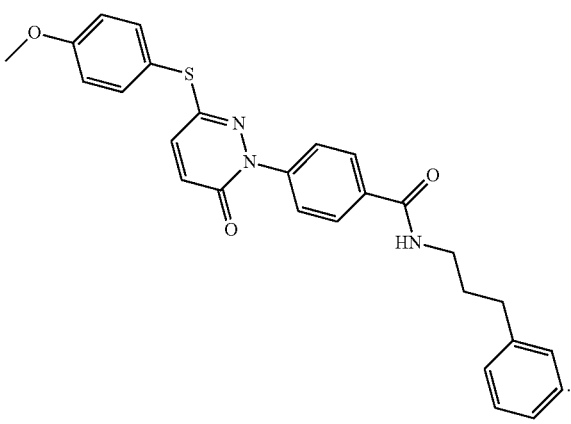 [SMILES: COc1ccc(Sc2ccc(=O)n(-c3ccc(C(=O)NCCCc4ccccc4)cc3)n2)cc1]

27. The pharmaceutical composition of claim 25, wherein the small molecule compound is a compound comprising the formula:

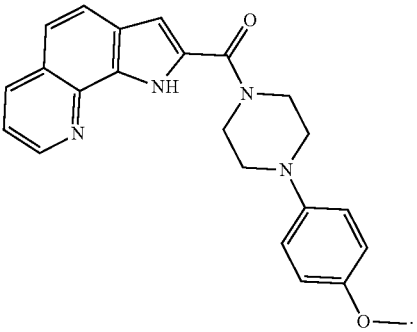 [SMILES: COc1ccc(N2CCN(C(=O)c3cc4ccc5cccnc5c4[nH]3)CC2)cc1]

28. The pharmaceutical composition of claim 25, wherein the small molecule inhibitor is a compound comprising the formula:

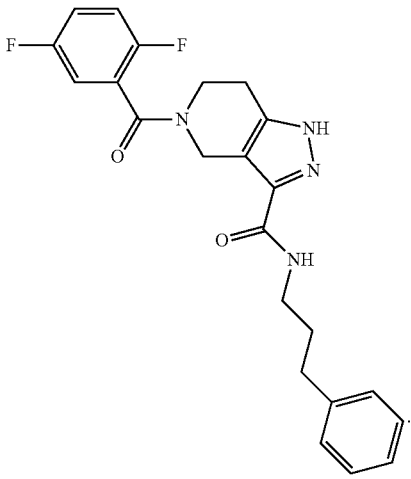 [SMILES: O=C(NCCCc1ccccc1)c1n[nH]c2c1CN(C(=O)c1cc(F)ccc1F)CC2]

29. The pharmaceutical composition of claim 26, wherein the pharmaceutical composition is formulated for oral, enteral, parenteral, intravenous, pulmonary, mucosal, submucosal or transdermal administration.

30. The pharmaceutical composition of claim 29, wherein the pharmaceutical composition is formulated in form of a capsule, tablet, pill, powder, granule, dragee, lozenge or bead for oral administration in immediate release, sustained release or controlled release form.

31. The pharmaceutical composition of claim 29, wherein the pharmaceutical composition is formulated in form of liquid emulsions, solutions, suspensions, syrups or elixirs for oral administration.

32. The pharmaceutical composition of claim 29, wherein the pharmaceutical composition is formulated in form of injectable depot for parenteral administration.

33. The pharmaceutical composition of claim 29, wherein the pharmaceutical composition is formulated in form of patch or hydrogel for transdermal application.

34. The pharmaceutical composition of claim 29, wherein the pharmaceutical composition contains one or more pharmaceutically acceptable excipients, diluents, adjuvants, stabilizers, emulsifiers, preservatives, colorants, buffers, flavor-imparting agents or pharmaceutically acceptable carriers suitable for oral, enteral, parenteral, intravenous or transdermal administration.

35. The pharmaceutical composition of claim 34, wherein the pharmaceutical composition further comprises one or more of a chemotherapeutic agent, an immunosuppressive agent, an immuno-stimulatory agent, an anti-pyretic agent, a cytotoxic agent, a nucleolytic compound, a radioactive isotope, a receptor, a pro-drug activating enzyme, an anti-inflammatory agent, an antibiotic, a protease inhibitor, a growth factor, an osteo-inductive factor, an antibacterial agent or an antifungal agent.

36. The pharmaceutical composition of claim 20, wherein the disease associated with uncontrolled inflammatory response is systemic juvenile idiopathic arthritis, Still's disease, Sjögren's syndrome or cancer.

\* \* \* \* \*